US012555668B2

(12) United States Patent
Cipollone et al.

(10) Patent No.: US 12,555,668 B2
(45) Date of Patent: Feb. 17, 2026

(54) RESPIRATORY THERAPY DATA MANAGEMENT SYSTEMS, DEVICES, AND METHODS

(71) Applicant: Ventec Life Systems, Inc., Bothell, WA (US)

(72) Inventors: Joseph Cipollone, Bothell, WA (US); Gregory A. McKeag, Kirkland, WA (US); Michael B. Holmes, Bothell, WA (US); Eric A. Harris, Seattle, WA (US); Christopher T. Kiple, Seattle, WA (US); Chris O. Brooks, Seattle, WA (US); Caro Minnick, Bellingham, WA (US)

(73) Assignee: Ventec Life Systems, Inc., Bothell, WA (US)

(*) Notice: Subject to any disclaimer, the term of this patent is extended or adjusted under 35 U.S.C. 154(b) by 760 days.

(21) Appl. No.: 17/520,616

(22) Filed: Nov. 5, 2021

(65) Prior Publication Data

US 2022/0148701 A1 May 12, 2022

Related U.S. Application Data

(60) Provisional application No. 63/158,266, filed on Mar. 8, 2021, provisional application No. 63/110,893, filed on Nov. 6, 2020.

(51) Int. Cl.

| | |
|---|---|
| ***G16H 20/40*** | (2018.01) |
| ***A61B 5/0205*** | (2006.01) |
| ***G16H 40/67*** | (2018.01) |

(52) U.S. Cl.

CPC ............ *G16H 20/40* (2018.01); *G16H 40/67* (2018.01); *A61B 5/0205* (2013.01)

(58) Field of Classification Search

CPC ...... G16H 20/40; G16H 40/67; A61B 5/0205; A61B 5/087; A61B 5/7264; A61B 5/091;

(Continued)

(56) References Cited

U.S. PATENT DOCUMENTS

| | | | |
|---|---|---|---|
| 3,191,596 | A | 6/1965 | Bird |
| 3,234,932 | A | 2/1966 | Bird |

(Continued)

FOREIGN PATENT DOCUMENTS

| | | | |
|---|---|---|---|
| CN | 103071215 | A | 5/2013 |
| CN | 107430641 | A | 12/2017 |

(Continued)

OTHER PUBLICATIONS

US 8,012,240 B2, 09/2011, Sprinkle (withdrawn)

(Continued)

*Primary Examiner* — Patrick Fernandes
(74) *Attorney, Agent, or Firm* — Perkins Coie LLP

(57) ABSTRACT

The present technology is directed to respiratory therapy data management systems, device, and methods. The systems can collect, store, monitor, report, and/or analyze patient treatment data associated with patient use of one or more respiratory therapy devices. The patient treatment data can include therapy data related to the use of multiple respiratory therapies, such as ventilation, oxygen, cough-assistance, suction, and nebulization. The patient treatment data may be collected from a plurality of respiratory devices associated with a particular patient, or from a single respiratory device associated with a particular patient. The system can generate customizable reports detailing the patient treatment data. The reports can summarize patient use, illustrate therapy trends, and/or provide therapy recommendations.

20 Claims, 15 Drawing Sheets

(58) Field of Classification Search
CPC ....... A61B 5/08; A61B 5/0836; A61B 5/4818; A61B 5/0816; A61B 5/082; A61M 16/107; A61M 2202/0208
See application file for complete search history.

(56) References Cited

U.S. PATENT DOCUMENTS 3,789,837 A 2/1974 Philips et al.
3,806,102 A 4/1974 Valenta et al.
3,875,626 A 4/1975 Tysk et al.
4,280,399 A 7/1981 Cunning
4,331,455 A 5/1982 Sato
4,357,936 A 11/1982 Ellestad et al.
4,367,767 A 1/1983 Hurd
4,386,945 A 6/1983 Gardner
4,401,116 A 8/1983 Fry et al.
4,417,573 A 11/1983 De Vries
4,425,914 A 1/1984 Ray et al.
4,449,990 A 5/1984 Tedford, Jr.
4,450,838 A 5/1984 Miodownik
4,459,982 A 7/1984 Fry
4,502,481 A 3/1985 Christian
4,502,873 A 3/1985 Mottram et al.
4,516,424 A 5/1985 Rowland
4,527,557 A 7/1985 Devries et al.
4,545,790 A 10/1985 Miller et al.
4,561,287 A 12/1985 Rowland
4,576,616 A 3/1986 Mottram et al.
4,602,653 A 7/1986 Ruiz-vela et al.
4,621,632 A 11/1986 Bartels et al.
4,627,860 A 12/1986 Rowland
4,637,386 A 1/1987 Baum
4,648,395 A 3/1987 Sato et al.
4,648,888 A 3/1987 Rowland
4,681,099 A 7/1987 Sato et al.
4,682,591 A 7/1987 Jones
4,702,240 A 10/1987 Chaoui
4,794,922 A 1/1989 Devries
4,807,616 A 2/1989 Adahan
4,813,979 A 3/1989 Miller et al.
4,869,733 A 9/1989 Stanford
4,880,443 A 11/1989 Miller et al.
4,905,685 A 3/1990 Olsson et al.
4,936,297 A 6/1990 Greiff et al.
4,941,469 A 7/1990 Adahan
4,971,609 A 11/1990 Pawlos
4,983,190 A 1/1991 Verrando et al.
4,993,269 A 2/1991 Guillaume et al.
5,002,591 A 3/1991 Stanford
5,014,694 A 5/1991 Devries
5,021,137 A 6/1991 Joshi et al.
5,024,219 A 6/1991 Dietz
5,034,023 A 7/1991 Thompson
5,071,453 A 12/1991 Hradek et al.
5,072,729 A 12/1991 Devries
5,101,656 A 4/1992 Miller
5,107,831 A 4/1992 Halpern et al.
5,127,400 A 7/1992 Devries et al.
5,129,924 A 7/1992 Schultz
5,134,329 A 7/1992 Lang
5,161,525 A 11/1992 Kimm et al.
5,166,563 A 11/1992 Bassine
5,169,506 A 12/1992 Michaels
5,186,793 A 2/1993 Michaels
5,265,594 A 11/1993 Olsson et al.
5,273,031 A 12/1993 Olsson et al.
5,275,642 A 1/1994 Bassine
5,296,110 A 3/1994 Tabatabaie-raissi
5,331,995 A 7/1994 Westfall et al.
5,335,426 A 8/1994 Settlemyer et al.
5,354,361 A 10/1994 Coffield
5,370,112 A 12/1994 Perkins
5,378,345 A 1/1995 Taylor et al.
5,397,443 A 3/1995 Michaels
5,400,777 A 3/1995 Olsson et al.
5,469,372 A 11/1995 Mcbrearty et al.
5,474,062 A 12/1995 Devires et al.
5,474,595 A 12/1995 Mccombs
5,494,028 A 2/1996 Devries et al.
5,497,767 A 3/1996 Olsson et al.
5,501,212 A 3/1996 Psaros
5,540,220 A 7/1996 Gropper et al.
5,540,233 A 7/1996 Larsson et al.
5,575,283 A 11/1996 Sjoestrand
5,578,115 A 11/1996 Cole
5,676,133 A 10/1997 Hickle et al.
5,694,924 A 12/1997 Cewers
5,694,926 A 12/1997 Devries et al.
5,701,883 A 12/1997 Hete et al.
5,706,801 A 1/1998 Remes et al.
5,720,277 A 2/1998 Olsson et al.
5,740,796 A 4/1998 Skog
5,743,253 A 4/1998 Castor et al.
5,746,806 A 5/1998 Aylsworth et al.
5,765,557 A 6/1998 Warters
5,765,558 A 6/1998 Psaros et al.
5,766,310 A 6/1998 Cramer
5,810,324 A 9/1998 Eriksson et al.
5,827,358 A 10/1998 Kulish et al.
5,845,633 A 12/1998 Psaros
5,849,219 A 12/1998 De Laat et al.
5,858,062 A 1/1999 Mcculloh et al.
5,858,063 A 1/1999 Cao et al.
5,862,802 A 1/1999 Bird
5,868,133 A 2/1999 Devries et al.
5,871,564 A 2/1999 Mccombs
5,875,777 A 3/1999 Eriksson
5,878,744 A 3/1999 Pfeiffer
5,881,722 A 3/1999 Devries et al.
5,893,944 A 4/1999 Dong
5,896,857 A 4/1999 Hely et al.
5,906,672 A 5/1999 Michaels et al.
5,917,135 A 6/1999 Michaels et al.
5,931,162 A 8/1999 Christian
5,937,853 A 8/1999 Stroem
5,948,142 A 9/1999 Holmes et al.
5,957,130 A 9/1999 Krahbichler et al.
5,968,236 A 10/1999 Bassine
5,988,165 A 11/1999 Richey, II et al.
5,997,617 A 12/1999 Czabala et al.
6,010,555 A 1/2000 Smolarek et al.
6,035,851 A 3/2000 Wallen
6,062,218 A 5/2000 Krahbichler et al.
6,068,680 A 5/2000 Kulish et al.
6,073,630 A 6/2000 Adahan
6,095,139 A 8/2000 Psaros
6,102,038 A 8/2000 Devries
6,112,744 A 9/2000 Hoegnelid
6,113,673 A 9/2000 Loutfy et al.
6,123,074 A 9/2000 Hete et al.
6,152,132 A 11/2000 Psaros
6,152,134 A 11/2000 Webber et al.
6,152,135 A 11/2000 Devries et al.
6,155,252 A 12/2000 Warters
6,156,100 A 12/2000 Conrad et al.
6,158,430 A 12/2000 Pfeiffer et al.
6,162,283 A 12/2000 Conrad et al.
6,176,897 B1 1/2001 Keefer
6,186,142 B1 2/2001 Schmidt et al.
6,189,532 B1 2/2001 Hely et al.
6,190,441 B1 2/2001 Czabala et al.
6,192,885 B1 2/2001 Jalde
6,217,635 B1 4/2001 Conrad et al.
6,234,170 B1 5/2001 Bergkvist
6,253,767 B1 7/2001 Mantz
6,263,873 B1 7/2001 Hedenberg
6,269,811 B1 8/2001 Duff
6,298,848 B1 10/2001 Skog
6,302,107 B1 10/2001 Richey, II et al.
6,344,069 B2 2/2002 Smolarek et al.
6,346,139 B1 2/2002 Czabala
6,348,082 B1 2/2002 Murdoch et al.
6,360,740 B1 3/2002 Ward et al.
6,386,235 B1 5/2002 Mcculloh et al.

(56) References Cited

U.S. PATENT DOCUMENTS

| | | | |
|---|---|---|---|
| 6,393,802 | B1 | 5/2002 | Bowser et al. |
| 6,394,089 | B1 | 5/2002 | Cantrill et al. |
| 6,395,065 | B1 | 5/2002 | Murdoch et al. |
| 6,412,483 | B1 | 7/2002 | Jones et al. |
| 6,446,630 | B1 | 9/2002 | Todd, Jr. |
| 6,471,744 | B1 | 10/2002 | Hill |
| 6,478,850 | B2 | 11/2002 | Warren |
| 6,478,857 | B2 | 11/2002 | Czabala |
| 6,497,755 | B2 | 12/2002 | Murdoch et al. |
| 6,514,318 | B2 | 2/2003 | Keefer |
| 6,514,319 | B2 | 2/2003 | Keefer et al. |
| 6,516,798 | B1 | 2/2003 | Davies |
| 6,520,176 | B1 | 2/2003 | Dubois et al. |
| 6,524,370 | B2 | 2/2003 | Maheshwary et al. |
| 6,526,970 | B2 | 3/2003 | Devries et al. |
| 6,532,956 | B2 | 3/2003 | Hill |
| 6,547,851 | B2 | 4/2003 | Warren |
| 6,551,384 | B1 | 4/2003 | Ackley et al. |
| 6,553,992 | B1 | 4/2003 | Berthon-jones et al. |
| 6,558,451 | B2 | 5/2003 | Mccombs et al. |
| 6,564,798 | B1 | 5/2003 | Jalde |
| 6,565,635 | B2 | 5/2003 | Keefer et al. |
| 6,595,213 | B2 | 7/2003 | Bennarsten |
| 6,601,583 | B2 | 8/2003 | Pessala et al. |
| 6,622,726 | B1 | 9/2003 | Du |
| 6,626,175 | B2 | 9/2003 | Jafari et al. |
| 6,629,525 | B2 | 10/2003 | Hill et al. |
| 6,640,807 | B2 | 11/2003 | Bennarsten |
| 6,641,644 | B2 | 11/2003 | Jagger et al. |
| 6,641,645 | B1 | 11/2003 | Lee et al. |
| 6,644,312 | B2 | 11/2003 | Berthon-jones et al. |
| 6,651,652 | B1 | 11/2003 | Waard |
| 6,651,658 | B1 | 11/2003 | Hill et al. |
| 6,651,692 | B2 | 11/2003 | Meckes et al. |
| 6,660,065 | B2 | 12/2003 | Byrd et al. |
| 6,668,828 | B1 | 12/2003 | Figley et al. |
| 6,679,258 | B1 | 1/2004 | Stroem |
| 6,691,702 | B2 | 2/2004 | Appel et al. |
| 6,694,978 | B1 | 2/2004 | Bennarsten |
| 6,702,880 | B2 | 3/2004 | Roberts et al. |
| 6,712,876 | B2 | 3/2004 | Cao et al. |
| 6,712,877 | B2 | 3/2004 | Cao et al. |
| 6,739,334 | B2 | 5/2004 | Valeij |
| 6,740,146 | B2 | 5/2004 | Simonds |
| 6,755,193 | B2 | 6/2004 | Berthon-jones et al. |
| 6,758,216 | B1 | 7/2004 | Berthon-jones et al. |
| 6,761,166 | B2 | 7/2004 | Ahlmen et al. |
| 6,764,534 | B2 | 7/2004 | Mccombs et al. |
| 6,782,888 | B1 | 8/2004 | Friberg et al. |
| 6,793,719 | B2 | 9/2004 | Kim et al. |
| 6,805,122 | B2 | 10/2004 | Richey, II et al. |
| 6,811,590 | B2 | 11/2004 | Lee et al. |
| 6,837,244 | B2 | 1/2005 | Yagi et al. |
| 6,845,773 | B2 | 1/2005 | Berthon-jones et al. |
| 6,860,858 | B2 | 3/2005 | Green et al. |
| 6,863,068 | B2 | 3/2005 | Jamison et al. |
| 6,866,700 | B2 | 3/2005 | Amann |
| 6,877,511 | B2 | 4/2005 | Devries et al. |
| 6,889,726 | B2 | 5/2005 | Richey, II et al. |
| 6,896,721 | B1 | 5/2005 | Lynn |
| 6,908,503 | B2 | 6/2005 | Mccombs et al. |
| 6,910,480 | B1 | 6/2005 | Berthon-jones |
| 6,923,180 | B2 | 8/2005 | Richey, II et al. |
| 6,935,460 | B2 | 8/2005 | Mccombs et al. |
| 6,949,133 | B2 | 9/2005 | Mccombs et al. |
| 6,997,881 | B2 | 2/2006 | Green et al. |
| 7,000,610 | B2 | 2/2006 | Bennarsten et al. |
| 7,032,592 | B2 | 4/2006 | Castor et al. |
| 7,040,318 | B2 | 5/2006 | Daescher et al. |
| 7,055,522 | B2 | 6/2006 | Berthon-jones |
| 7,066,985 | B2 | 6/2006 | Deane et al. |
| 7,077,133 | B2 | 7/2006 | Yagi et al. |
| 7,081,745 | B2 | 7/2006 | Haveri |
| 7,089,937 | B2 | 8/2006 | Berthon-jones et al. |
| 7,094,275 | B2 | 8/2006 | Keefer et al. |
| 7,096,866 | B2 | 8/2006 | Be'eri et al. |
| 7,100,609 | B2 | 9/2006 | Berthon-jones et al. |
| 7,105,038 | B2 | 9/2006 | Lee et al. |
| 7,121,276 | B2 | 10/2006 | Jagger et al. |
| 7,121,277 | B2 | 10/2006 | Stroem |
| 7,135,059 | B2 | 11/2006 | Deane et al. |
| 7,156,903 | B2 | 1/2007 | Mccombs |
| 7,171,963 | B2 | 2/2007 | Jagger et al. |
| 7,179,326 | B2 | 2/2007 | Nakamura et al. |
| 7,188,621 | B2 | 3/2007 | DeVries et al. |
| 7,213,468 | B2 | 5/2007 | Fujimoto |
| 7,219,666 | B2 | 5/2007 | Friberg et al. |
| 7,222,623 | B2 | 5/2007 | Devries et al. |
| 7,250,073 | B2 | 7/2007 | Keefer et al. |
| 7,255,103 | B2 | 8/2007 | Bassin |
| 7,279,029 | B2 | 10/2007 | Occhialini et al. |
| 7,294,170 | B2 | 11/2007 | Richey, II et al. |
| 7,329,304 | B2 | 2/2008 | Bliss et al. |
| 7,347,207 | B2 | 3/2008 | Ahlmen et al. |
| 7,350,521 | B2 | 4/2008 | Whitley et al. |
| 7,367,337 | B2 | 5/2008 | Berthon-jones et al. |
| 7,368,005 | B2 | 5/2008 | Bliss et al. |
| RE40,402 | E | 6/2008 | Leonhardt et al. |
| 7,402,193 | B2 | 7/2008 | Bliss et al. |
| 7,406,966 | B2 | 8/2008 | Wondka |
| 7,427,315 | B2 | 9/2008 | Dolensky et al. |
| 7,428,902 | B2 | 9/2008 | Du et al. |
| 7,429,289 | B2 | 9/2008 | Dolensky et al. |
| 7,431,032 | B2 | 10/2008 | Jagger et al. |
| 7,438,745 | B2 | 10/2008 | Deane et al. |
| 7,445,546 | B2 | 11/2008 | Hondmann et al. |
| 7,445,663 | B1 | 11/2008 | Hunter et al. |
| 7,455,717 | B2 | 11/2008 | Sprinkle |
| 7,473,299 | B2 | 1/2009 | Occhialini et al. |
| 7,491,261 | B2 | 2/2009 | Warren et al. |
| 7,497,215 | B1 | 3/2009 | Nguyen et al. |
| 7,510,601 | B2 | 3/2009 | Whitley et al. |
| 7,517,385 | B2 | 4/2009 | Winter |
| 7,524,365 | B2 | 4/2009 | Lin |
| 7,527,053 | B2 | 5/2009 | Devries et al. |
| 7,533,872 | B2 | 5/2009 | Lee et al. |
| 7,550,031 | B2 | 6/2009 | Hunter et al. |
| 7,550,036 | B2 | 6/2009 | Lee et al. |
| 7,556,670 | B2 | 7/2009 | Aylsworth et al. |
| 7,559,326 | B2 | 7/2009 | Smith et al. |
| 7,585,351 | B2 | 9/2009 | Deane et al. |
| 7,590,551 | B2 | 9/2009 | Auer |
| 7,604,004 | B2 | 10/2009 | Jagger et al. |
| 7,604,005 | B2 | 10/2009 | Jagger et al. |
| 7,628,151 | B2 | 12/2009 | Bassin |
| 7,637,989 | B2 | 12/2009 | Bong |
| 7,655,059 | B2 | 2/2010 | Wang et al. |
| 7,655,063 | B2 | 2/2010 | Wang et al. |
| 7,682,428 | B2 | 3/2010 | Nawata et al. |
| 7,682,429 | B2 | 3/2010 | Dolensky et al. |
| 7,686,870 | B1 | 3/2010 | Deane et al. |
| 7,704,304 | B2 | 4/2010 | Warren et al. |
| 7,708,802 | B1 | 5/2010 | Deane et al. |
| 7,708,818 | B2 | 5/2010 | Clark |
| 7,717,981 | B2 | 5/2010 | Labuda et al. |
| 7,722,700 | B2 | 5/2010 | Sprinkle |
| 7,727,160 | B2 | 6/2010 | Green et al. |
| 7,730,887 | B2 | 6/2010 | Deane et al. |
| 7,753,996 | B1 | 7/2010 | Deane et al. |
| 7,758,672 | B2 | 7/2010 | Lee et al. |
| 7,763,103 | B2 | 7/2010 | Dolensky et al. |
| 7,766,010 | B2 | 8/2010 | Jagger et al. |
| 7,771,511 | B2 | 8/2010 | Dolensky |
| 7,780,768 | B2 | 8/2010 | Taylor et al. |
| 7,780,769 | B2 | 8/2010 | Dolensky et al. |
| 7,794,522 | B2 | 9/2010 | Bliss et al. |
| 7,828,878 | B2 | 11/2010 | Zhong et al. |
| 7,837,761 | B2 | 11/2010 | Bliss et al. |
| 7,841,343 | B2 | 11/2010 | Deane et al. |
| 7,849,854 | B2 | 12/2010 | Devries et al. |
| 7,857,894 | B2 | 12/2010 | Taylor et al. |
| 7,861,716 | B2 | 1/2011 | Borrello |
| 7,866,315 | B2 | 1/2011 | Jagger et al. |
| 7,874,290 | B2 | 1/2011 | Chalvignac |

(56) References Cited

U.S. PATENT DOCUMENTS 7,875,105 B2 1/2011 Chambers et al.
7,892,322 B2 2/2011 Ono et al.
7,909,034 B2 3/2011 Sinderby et al.
7,914,459 B2 3/2011 Green et al.
7,918,925 B2 4/2011 Dolensky et al.
7,922,789 B1 4/2011 Deane et al.
7,934,499 B2 5/2011 Berthon-jones
7,954,493 B2 6/2011 Nawata
8,006,692 B2 8/2011 Smith et al.
8,016,916 B2 9/2011 Ono et al.
8,016,918 B2 9/2011 Labuda et al.
8,016,925 B2 9/2011 Mccombs et al.
8,020,553 B2 9/2011 Jagger et al.
8,051,852 B2 11/2011 Bassin
8,062,003 B2 11/2011 Goertzen
8,070,853 B2 12/2011 Sprinkle
8,070,864 B2 12/2011 Uchiyama et al.
8,070,922 B2 12/2011 Nelson et al.
8,075,676 B2 12/2011 Thompson et al.
8,100,125 B2 1/2012 Duquette et al.
8,118,024 B2 2/2012 Devries et al.
8,122,885 B2 2/2012 Berthon-jones et al.
8,123,497 B2 2/2012 Richey, II et al.
8,142,544 B2 3/2012 Taylor et al.
8,146,596 B2 4/2012 Smith et al.
8,147,597 B2 4/2012 Dolensky et al.
8,156,937 B2 4/2012 Devries et al.
8,167,988 B2 5/2012 Dolensky et al.
8,192,526 B2 6/2012 Zhong et al.
8,210,205 B2 7/2012 Michaels
8,225,789 B2 7/2012 Berthon-jones
8,226,745 B2 7/2012 Siew-wah et al.
8,236,095 B1 8/2012 Bassine
8,256,419 B2 9/2012 Sinderby et al.
8,257,473 B2 9/2012 Mccombs et al.
8,280,498 B2 10/2012 Jalde
8,282,717 B2 10/2012 Chambers et al.
8,297,279 B2 10/2012 Devries et al.
8,337,599 B2 12/2012 Kiritake
8,343,259 B2 1/2013 Knaebel
8,349,053 B2 1/2013 Lee et al.
8,361,204 B1 1/2013 Bassine
8,366,815 B2 2/2013 Taylor et al.
8,371,298 B2 2/2013 Hallback et al.
8,375,944 B2 2/2013 Kwok
8,377,180 B2 2/2013 Maeda et al.
8,377,181 B2 2/2013 Taylor et al.
8,388,548 B2 3/2013 Green et al.
8,388,745 B1 3/2013 Pelletier et al.
8,400,290 B2 3/2013 Baker, Jr.
8,418,691 B2 4/2013 Jafari et al.
8,418,692 B2 4/2013 Sanchez
8,424,520 B2 4/2013 Thiessen
8,424,521 B2 4/2013 Jafari et al.
8,428,672 B2 4/2013 Sherman et al.
8,434,480 B2 5/2013 Jafari et al.
8,434,482 B2 5/2013 Borrello
8,434,488 B2 5/2013 Li et al.
8,435,013 B2 5/2013 Kondou et al.
8,440,004 B2 5/2013 Taylor et al.
8,443,294 B2 5/2013 Skidmore et al.
8,448,640 B2 5/2013 Bassin
8,448,641 B2 5/2013 Jafari et al.
8,469,026 B2 6/2013 Blomberg et al.
8,522,780 B2 9/2013 Devries et al.
8,539,952 B2 9/2013 Carbone et al.
8,627,819 B2 1/2014 Devries et al.
8,683,997 B2 4/2014 Devries et al.
8,770,191 B2 7/2014 Tham
8,844,530 B2 9/2014 Birnkrant
9,126,002 B2 9/2015 Devries et al.
9,345,851 B2 5/2016 Kim et al.
9,504,799 B2 11/2016 Hardin et al.
9,522,248 B2 12/2016 Martin
9,956,371 B2 5/2018 DeVries
10,046,134 B2 8/2018 DeVries
10,105,509 B2 10/2018 DeVries
10,245,406 B2 4/2019 Devries
10,315,002 B2 6/2019 Devries et al.
10,350,377 B2 7/2019 Fiorenza
10,518,059 B2 12/2019 Cipollone et al.
10,758,699 B2 9/2020 Cipollone et al.
10,773,049 B2 9/2020 Gaw et al.
11,191,915 B2 12/2021 Ahmad
2002/0005197 A1 1/2002 DeVries
2002/0053286 A1 5/2002 Czabala
2002/0092420 A1 7/2002 Jagger et al.
2002/0121278 A1 9/2002 Hete
2003/0000528 A1* 1/2003 Eklund ............. A61M 16/0051 128/204.23
2003/0000531 A1 1/2003 Tuck
2003/0010208 A1 1/2003 Jagger et al.
2003/0024766 A1 2/2003 Briscoe
2003/0051729 A1 3/2003 Be'eri et al.
2003/0111077 A1 6/2003 Hooser
2003/0131848 A1 7/2003 Stenzler
2003/0196550 A1 10/2003 Keefer et al.
2003/0200865 A1 10/2003 Mccombs et al.
2003/0230308 A1 12/2003 Linden
2004/0021108 A1 2/2004 Hallback et al.
2004/0231913 A1 11/2004 Mccombs et al.
2005/0012657 A1 1/2005 Mohan
2005/0045040 A1 3/2005 Mccombs
2005/0065572 A1 3/2005 Hartlety et al.
2005/0072298 A1 4/2005 Deane et al.
2005/0072306 A1 4/2005 Deane et al.
2005/0072423 A1 4/2005 Deane et al.
2005/0072426 A1 4/2005 Deane et al.
2005/0103341 A1 5/2005 Deane et al.
2005/0112013 A1 5/2005 Devries et al.
2005/0217481 A1 10/2005 Dunne et al.
2005/0242946 A1* 11/2005 Hubbard, Jr. .......... A61B 5/002 600/300
2005/0257686 A1 11/2005 Occhialini et al.
2005/0274381 A1 12/2005 Deane et al.
2005/0274815 A1 12/2005 Bergholtz et al.
2006/0011065 A1 1/2006 Hastings
2006/0042631 A1 3/2006 Martin et al.
2006/0064802 A1 3/2006 Damrath et al.
2006/0086251 A1 4/2006 Sprinkle
2006/0102181 A1 5/2006 Mccombs et al.
2006/0107947 A1 5/2006 Rist
2006/0117957 A1 6/2006 Mccombs et al.
2006/0137522 A1 6/2006 Nishimura et al.
2006/0174871 A1 8/2006 Jagger et al.
2006/0174875 A1 8/2006 Jagger et al.
2006/0174877 A1 8/2006 Jagger et al.
2006/0230924 A1 10/2006 Deane et al.
2006/0230929 A1 10/2006 Bliss et al.
2006/0230931 A1 10/2006 Bliss et al.
2006/0230939 A1 10/2006 Bliss et al.
2006/0266357 A1 11/2006 Mccombs et al.
2006/0283325 A1 12/2006 Sugano
2006/0283447 A1 12/2006 Dhuper et al.
2007/0031302 A1 2/2007 Wittrup et al.
2007/0056583 A1 3/2007 Jagger et al.
2007/0056584 A1 3/2007 Jagger et al.
2007/0084342 A1 4/2007 Hunter et al.
2007/0084349 A1 4/2007 Calkins et al.
2007/0101999 A1 5/2007 Duquette et al.
2007/0135757 A1 6/2007 Acker
2007/0144521 A1 6/2007 Devries et al.
2007/0148016 A1 6/2007 Crawford et al.
2007/0169623 A1 7/2007 Lee et al.
2007/0199566 A1 8/2007 Be
2007/0214955 A1 9/2007 Aylsworth et al.
2007/0227360 A1 10/2007 Atlas et al.
2007/0227540 A1 10/2007 Ljungberg et al.
2007/0272243 A1 11/2007 Sherman et al.
2007/0289446 A1 12/2007 Occhialini et al.
2008/0000477 A1 1/2008 Huster et al.
2008/0004566 A1 1/2008 Sloan
2008/0028933 A1 2/2008 Ross et al.
2008/0034975 A1 2/2008 Chambers et al.

(56) References Cited

U.S. PATENT DOCUMENTS

| | | | |
|---|---|---|---|
| 2008/0053441 | A1 | 3/2008 | Gottlib |
| 2008/0066616 | A1 | 3/2008 | Sprinkle |
| 2008/0066741 | A1 | 3/2008 | LeMahieu et al. |
| 2008/0087170 | A1 | 4/2008 | Deane et al. |
| 2008/0092892 | A1 | 4/2008 | Boyle et al. |
| 2008/0092893 | A1 | 4/2008 | Boyle et al. |
| 2008/0110338 | A1 | 5/2008 | Taylor et al. |
| 2008/0110461 | A1 | 5/2008 | Mulqueeny et al. |
| 2008/0135044 | A1 | 6/2008 | Freitag et al. |
| 2008/0185544 | A1 | 8/2008 | Yeh |
| 2008/0196580 | A1 | 8/2008 | Bliss et al. |
| 2008/0202337 | A1 | 8/2008 | Taylor et al. |
| 2008/0202508 | A1 | 8/2008 | Mcclain et al. |
| 2008/0251071 | A1 | 10/2008 | Armitstead et al. |
| 2008/0257145 | A1 | 10/2008 | Sprinkle et al. |
| 2008/0257349 | A1 | 10/2008 | Hedner et al. |
| 2008/0282880 | A1 | 11/2008 | Bliss et al. |
| 2008/0295839 | A1 | 12/2008 | Habashi |
| 2008/0302362 | A1 | 12/2008 | Kwok |
| 2008/0302363 | A1 | 12/2008 | Kroupa |
| 2008/0314385 | A1 | 12/2008 | Brunner et al. |
| 2008/0315441 | A1 | 12/2008 | Lee et al. |
| 2009/0007912 | A1 | 1/2009 | Lindell et al. |
| 2009/0025560 | A1 | 1/2009 | Takemasa |
| 2009/0025564 | A1 | 1/2009 | Kuwabara |
| 2009/0044698 | A1 | 2/2009 | Meacham |
| 2009/0065007 | A1 | 3/2009 | Wilkinson et al. |
| 2009/0065526 | A1 | 3/2009 | Sprinkle |
| 2009/0071333 | A1 | 3/2009 | Labuda et al. |
| 2009/0078251 | A1 | 3/2009 | Zucchi et al. |
| 2009/0084381 | A1 | 4/2009 | Devries et al. |
| 2009/0101147 | A1 | 4/2009 | Landis et al. |
| 2009/0107500 | A1 | 4/2009 | Edwards |
| 2009/0133368 | A1 | 5/2009 | Calkins et al. |
| 2009/0133694 | A1 | 5/2009 | Solci et al. |
| 2009/0145428 | A1 | 6/2009 | Sward et al. |
| 2009/0167698 | A1 | 7/2009 | Altas et al. |
| 2009/0188500 | A1 | 7/2009 | Faram |
| 2009/0188502 | A1 | 7/2009 | Tiedje |
| 2009/0211448 | A1 | 8/2009 | Mcclain |
| 2009/0229459 | A1 | 9/2009 | Warren et al. |
| 2009/0250059 | A1 | 10/2009 | Allum et al. |
| 2009/0301477 | A1 | 12/2009 | Pierro et al. |
| 2009/0308396 | A1 | 12/2009 | Mcclain |
| 2010/0024819 | A1 | 2/2010 | Tiedje |
| 2010/0051030 | A1 | 3/2010 | Richard et al. |
| 2010/0052293 | A1 | 3/2010 | Brooks et al. |
| 2010/0071693 | A1 | 3/2010 | Allum et al. |
| 2010/0078018 | A1 | 4/2010 | Heinonen |
| 2010/0095841 | A1 | 4/2010 | Naheiri |
| 2010/0116270 | A1 | 5/2010 | Branson et al. |
| 2010/0122699 | A1 | 5/2010 | Birnkrant |
| 2010/0126249 | A1 | 5/2010 | Matsuzaki |
| 2010/0154797 | A1 | 6/2010 | Landis et al. |
| 2010/0229867 | A1 | 9/2010 | Bertinetti et al. |
| 2010/0275921 | A1 | 11/2010 | Schindhelm et al. |
| 2010/0282084 | A1 | 11/2010 | Hansen et al. |
| 2010/0288279 | A1 | 11/2010 | Seiver et al. |
| 2010/0294127 | A1 | 11/2010 | Dolensky |
| 2011/0000489 | A1 | 1/2011 | Laksov et al. |
| 2011/0030684 | A1 | 2/2011 | Wilkinson et al. |
| 2011/0030685 | A1 | 2/2011 | Wilkinson et al. |
| 2011/0030686 | A1 | 2/2011 | Wilkinson et al. |
| 2011/0030687 | A1 | 2/2011 | Wilkinson et al. |
| 2011/0030689 | A1 | 2/2011 | Wilkinson et al. |
| 2011/0057651 | A1 | 3/2011 | Duric et al. |
| 2011/0067699 | A1 | 3/2011 | Caruso et al. |
| 2011/0073107 | A1 | 3/2011 | Rodman et al. |
| 2011/0073115 | A1 | 3/2011 | Wood et al. |
| 2011/0113964 | A1 | 5/2011 | Chambers et al. |
| 2011/0154986 | A1 | 6/2011 | Lee et al. |
| 2011/0192122 | A1 | 8/2011 | Whitesel et al. |
| 2011/0197882 | A1 | 8/2011 | Truschel et al. |
| 2011/0197883 | A1 | 8/2011 | Mcdaniel et al. |
| 2011/0197884 | A1 | 8/2011 | Duff et al. |
| 2011/0197887 | A1 | 8/2011 | Truschel et al. |
| 2011/0209706 | A1 | 9/2011 | Truschel et al. |
| 2011/0209707 | A1 | 9/2011 | Terhark |
| 2011/0220107 | A1 | 9/2011 | Kimm et al. |
| 2011/0232483 | A1 | 9/2011 | Haberland et al. |
| 2011/0232645 | A1 | 9/2011 | Smith |
| 2011/0247616 | A1 | 10/2011 | Von Hollen et al. |
| 2011/0247620 | A1 | 10/2011 | Armstrong et al. |
| 2011/0247621 | A1 | 10/2011 | Richard et al. |
| 2011/0247622 | A1 | 10/2011 | Schneider et al. |
| 2011/0259334 | A1 | 10/2011 | Alfieri et al. |
| 2011/0297153 | A1 | 12/2011 | Grimsey |
| 2011/0303223 | A1 | 12/2011 | Kane et al. |
| 2011/0315140 | A1 | 12/2011 | Shuman |
| 2012/0000462 | A1 | 1/2012 | Edwards et al. |
| 2012/0006199 | A1 | 1/2012 | Mccombs et al. |
| 2012/0006326 | A1 | 1/2012 | Ahmad |
| 2012/0012109 | A1 | 1/2012 | Chalvignac |
| 2012/0017909 | A1 | 1/2012 | Porges et al. |
| 2012/0027628 | A1 | 2/2012 | Ogawa |
| 2012/0037159 | A1 | 2/2012 | Mulqueeny et al. |
| 2012/0055340 | A1 | 3/2012 | Wilkinson et al. |
| 2012/0055474 | A1 | 3/2012 | Wilkinson |
| 2012/0055475 | A1 | 3/2012 | Wilkinson |
| 2012/0055477 | A1 | 3/2012 | Wilkinson |
| 2012/0055480 | A1 | 3/2012 | Wilkinson |
| 2012/0055482 | A1 | 3/2012 | Wilkinson |
| 2012/0055483 | A1 | 3/2012 | Wilkinson et al. |
| 2012/0060840 | A1 | 3/2012 | Refsland et al. |
| 2012/0125336 | A1 | 5/2012 | Berthon-jones et al. |
| 2012/0125337 | A1 | 5/2012 | Asanoi |
| 2012/0152248 | A1 | 6/2012 | Richey, II et al. |
| 2012/0167883 | A1 | 7/2012 | Taylor et al. |
| 2012/0167886 | A1 | 7/2012 | Taylor et al. |
| 2012/0167887 | A1 | 7/2012 | Taylor et al. |
| 2012/0167888 | A1 | 7/2012 | Taylor et al. |
| 2012/0177546 | A1 | 7/2012 | Hilbig |
| 2012/0192862 | A1 | 8/2012 | Lewis et al. |
| 2012/0192864 | A1 | 8/2012 | Galbraith et al. |
| 2012/0192867 | A1 | 8/2012 | Lewis et al. |
| 2012/0247329 | A1 | 10/2012 | Hilbig |
| 2012/0266883 | A1 | 10/2012 | Taylor et al. |
| 2012/0285460 | A1 | 11/2012 | Smith et al. |
| 2012/0285543 | A1 | 11/2012 | Michaels |
| 2012/0291884 | A1 | 11/2012 | Yamaura et al. |
| 2012/0304867 | A1 | 12/2012 | Watanabe et al. |
| 2012/0308779 | A1 | 12/2012 | Klee et al. |
| 2012/0318145 | A1 | 12/2012 | Hilbig et al. |
| 2013/0008438 | A1 | 1/2013 | Sugawara et al. |
| 2013/0008444 | A1 | 1/2013 | Chalvignac et al. |
| 2013/0025591 | A1 | 1/2013 | Clark et al. |
| 2013/0030831 | A1 * | 1/2013 | Powell .................. G16H 10/60 705/2 |
| 2013/0031784 | A1 | 2/2013 | Chambers et al. |
| 2013/0032148 | A1 | 2/2013 | Neely |
| 2013/0081617 | A1 | 4/2013 | Cavendish |
| 2013/0087145 | A1 | 4/2013 | Koebrich et al. |
| 2013/0087146 | A1 | 4/2013 | Callaghan et al. |
| 2013/0092159 | A1 | 4/2013 | Ulrichskoetter et al. |
| 2013/0098361 | A1 | 4/2013 | Koebrich et al. |
| 2013/0104898 | A1 | 5/2013 | Berthon-jones |
| 2013/0125891 | A1 | 5/2013 | Eddy |
| 2013/0167843 | A1 | 7/2013 | Kimm et al. |
| 2013/0186400 | A1 | 7/2013 | Jafari et al. |
| 2013/0186401 | A1 | 7/2013 | Jafari et al. |
| 2013/0199520 | A1 | 8/2013 | Dhuper et al. |
| 2013/0220325 | A1 | 8/2013 | Davis et al. |
| 2013/0255689 | A1 | 10/2013 | Kim et al. |
| 2013/0272905 | A1 | 10/2013 | Shelke |
| 2013/0276789 | A1 | 10/2013 | Garde et al. |
| 2013/0310713 | A1 | 11/2013 | Weber et al. |
| 2013/0312757 | A1 | 11/2013 | Gragg et al. |
| 2014/0007878 | A1 | 1/2014 | Armistead et al. |
| 2014/0116441 | A1 | 5/2014 | Mcdaniel |
| 2014/0150789 | A1 | 6/2014 | Flanagan et al. |
| 2014/0150791 | A1 | 6/2014 | Birnkrant et al. |
| 2014/0150792 | A1 | 6/2014 | Christopher et al. |
| 2014/0166009 | A1 | 6/2014 | Flanagan et al. |
| 2014/0216446 | A1 | 8/2014 | Wruck |

(56) References Cited

U.S. PATENT DOCUMENTS

| | | | |
|---|---|---|---|
| 2014/0318535 | A1 | 10/2014 | Bullock |
| 2014/0373835 | A1 | 12/2014 | Ahmad et al. |
| 2015/0000654 | A1 | 1/2015 | Martin |
| 2015/0000660 | A1 | 1/2015 | Martin |
| 2015/0027444 | A1 | 1/2015 | Col, Jr. |
| 2015/0101610 | A1 | 4/2015 | Nitta |
| 2015/0224278 | A1 | 8/2015 | Addington et al. |
| 2015/0283352 | A1 | 10/2015 | Karkkainen |
| 2015/0320962 | A1 | 11/2015 | Bafile |
| 2016/0095997 | A1 | 4/2016 | Kapust et al. |
| 2016/0135734 | A1* | 5/2016 | Schindhelm ......... A61B 5/4836 607/42 |
| 2016/0243330 | A1 | 8/2016 | Destefano |
| 2016/0279369 | A1 | 9/2016 | Cipollone |
| 2016/0279378 | A1 | 9/2016 | Cipollone et al. |
| 2017/0000968 | A1 | 1/2017 | Harrington et al. |
| 2017/0232214 | A1* | 8/2017 | Walsh ................. A61M 16/021 128/202.22 |
| 2017/0361058 | A1 | 12/2017 | Gaw et al. |
| 2018/0085541 | A1 | 3/2018 | Ye et al. |
| 2019/0054268 | A1 | 2/2019 | DeVries |
| 2019/0143056 | A1 | 5/2019 | Steinhauer et al. |
| 2020/0053086 | A1 | 2/2020 | Schwaibold et al. |
| 2021/0252243 | A1 | 8/2021 | Barlow et al. |

FOREIGN PATENT DOCUMENTS

| | | | |
|---|---|---|---|
| EP | 0937478 | B1 | 8/2003 |
| GB | 2164568 | A | 3/1986 |
| GB | 2485417 | A | 5/2012 |
| JP | H11-192410 | A | 7/1999 |
| JP | H11-210927 | A | 8/1999 |
| JP | 2000024110 | A | 1/2000 |
| JP | 2000102617 | A | 4/2000 |
| JP | 2000300673 | A | 10/2000 |
| JP | 2001507982 | A | 6/2001 |
| JP | 2002136598 | A | 5/2002 |
| JP | 2003156174 | A | 5/2003 |
| JP | 2007117273 | A | 5/2007 |
| JP | 2008501445 | A | 1/2008 |
| JP | 2008539841 | A | 11/2008 |
| JP | 2010535078 | A | 11/2010 |
| JP | 2012508074 | A | 4/2012 |
| JP | 201418030 | A | 9/2014 |
| JP | 2015080699 | A | 4/2015 |
| WO | 1998022172 | A | 5/1998 |
| WO | 1998026830 | A | 6/1998 |
| WO | 1999008738 | A1 | 2/1999 |
| WO | 2000038772 | A1 | 7/2000 |
| WO | 2003008017 | A2 | 1/2003 |
| WO | 2003045486 | A1 | 6/2003 |
| WO | 2006102345 | A1 | 9/2006 |
| WO | 2006121980 | A2 | 11/2006 |
| WO | 2010054323 | A3 | 5/2010 |
| WO | 2010141983 | A1 | 12/2010 |
| WO | 2011161060 | A1 | 12/2011 |
| WO | 2012052903 | A1 | 4/2012 |
| WO | 2013033589 | A1 | 3/2013 |
| WO | 2013067592 | A1 | 5/2013 |
| WO | 2013140321 | A1 | 9/2013 |
| WO | 2013157517 | A1 | 10/2013 |
| WO | 2013164733 | A1 | 11/2013 |
| WO | 2014059405 | A1 | 4/2014 |
| WO | 2014089188 | A1 | 6/2014 |
| WO | 2014176454 | A1 | 10/2014 |
| WO | 2015015394 | A1 | 2/2015 |
| WO | 2015126853 | A1 | 8/2015 |
| WO | 2016019304 | A1 | 2/2016 |
| WO | 2016067147 | A1 | 5/2016 |
| WO | 2017149532 | A1 | 9/2017 |
| WO | 2020092701 | A2 | 5/2020 |

OTHER PUBLICATIONS

Extended European Search Report mailed on Aug. 7, 2024 in European Patent Application No. 21890212.0, 8 pages.

Branson, D R. et al., Branson, D. Richard et al., "Maximizing Oxygen Delivery During Mechanical Ventilation with a Portable Oxygen Concentrator," The Journal of TRAUMA® Injury, Infection, and Critical Care, vol. 69, No. 1, July Supplement 2010, 7 pages., Jul. 2010, 7 pages.

Gangidine et al., "System Design Verification for Closed Loop Control of Oxygenation With Concentrator Integration," Military Medicine, 2016, vol. 181(5):177-183.

Gustafson, et al., Gustafson et al., "Pulse Dose Delivery of Oxygen in Mechanically Ventilated Pigs with Acute Lung Injury," The Journal of Trauma and Acute Care Surgery, 75(5), Nov. 2013, pp. 775-779., 5 pages.

Rodriguez et al., "Maximizing Oxygen Delivery During Mechanical Ventilation with a Portable Oxygen Concentrator," Journal of Trauma-Injury Infection & Critical Care, 69(1), Jul. 2020, pp. S87-S93.

International Search Report and Written Opinion mailed on Jan. 27, 2022 in International Patent Application No. PCT/US2021/058363, 12 pages.

CN Patent Application No. 202180089282.5—Chinese Office Action and Search Report, dated Aug. 23, 2025, with English Translation, 37 pages.

JP Patent Application No. 2023-526016—Japanese Office Action and Search Report, issued Sep. 25, 2025, with English Translation, 16 pages.

* cited by examiner

500

| Alarm | Total | Duration (sec.) 0-20 | 20-40 | 40-60 | 60+ |
|---|---|---|---|---|---|
| High Pressure | 71 | 71 | | | |
| Low Minute Volume | 3 | 2 | 1 | | |
| Patient Circuit Disconnect | 3 | 3 | | | |

700

Therapy Log

| Therapy | Start | End | Duration |
|---|---|---|---|
| **Ventilation Therapy** Preset 1 - "DAY" | 6/18 11:25:28 | 6/18 11:29:08 | 0:03:40 |
| **Ventilation Therapy** Preset 1 - "DAY" | 6/18 11:30:47 | 6/18 13:33:07 | 2:02:20 |
| **Cough Therapy** Preset 1 - "Preset 1" | 6/18 11:31:05 | 6/18 11:31:21 | 0:00:16 |
| **Suction Therapy** Suction: -192 mmHg | 6/18 11:31:05 | 6/18 11:31:50 | 0:00:45 |
| **Nebulizer Therapy (Internal)** | 6/18 11:31:51 | 6/18 11:36:15 | 0:04:24 |
| **Cough Therapy** Preset 2 - "Preset 2" | 6/18 11:32:29 | 6/18 11:32:53 | 0:00:24 |
| **Ventilation Therapy** Preset 3 - "MOBILE" | 6/18 13:33:07 | 6/18 16:21:48 | 2:48:41 |
| **Cough Therapy** Preset 1 - "Preset 1" | 6/18 13:34:14 | 6/18 13:34:30 | 0:00:16 |
| **Suction Therapy** Suction: -178 mmHg | 6/18 13:34:14 | 6/18 13:36:31 | 0:02:17 |
| **Nebulizer Therapy (Internal)** | 6/18 13:39:01 | 6/18 13:39:32 | 0:00:31 |
| **Cough Therapy** Preset 1 - "Preset 1" | 6/18 16:19:21 | 6/18 16:19:44 | 0:00:23 |
| **Suction Therapy** Suction: -180 mmHg | 6/18 16:19:21 | 6/18 16:21:45 | 0:02:24 |
| **Ventilation Therapy** Preset 2 - "NIGHT" | 6/18 16:21:48 | 6/18 20:21:45 | 3:59:57 |
| **Nebulizer Therapy (Internal)** | 6/18 16:27:56 | 6/18 16:29:34 | 0:01:38 |
| **Cough Therapy** Preset 1 - "Preset 1" | 6/18 16:28:42 | 6/18 16:29:05 | 0:00:23 |
| **Suction Therapy** Suction: -180 mmHg | 6/18 16:28:42 | 6/18 16:29:32 | 0:00:50 |
| **Ventilation Therapy** Preset 1 - "DAY" | 6/18 16:21:45 | 6/18 11:03:41 | 14:41:56 |
| **Nebulizer Therapy (Internal)** | 6/18 20:24:06 | 6/18 20:47:15 | 0:23:09 |
| **Cough Therapy** Preset 1 - "Preset 1" | 6/18 20:25:13 | 6/18 20:25:35 | 0:00:22 |

Trend Summary

*FIG. 7*

RESPIRATORY THERAPY DATA MANAGEMENT SYSTEMS, DEVICES, AND METHODS

CROSS-REFERENCE TO RELATED APPLICATIONS

The present application claims priority to U.S. Provisional Application No. 63/110,893, filed Nov. 6, 2020, and titled " RESPIRATORY THERAPY DATA MANAGEMENT SYSTEMS, DEVICES, AND METHODS," and U.S. Provisional Application No. 63/158,266, filed Mar. 8, 2021, and titled " RESPIRATORY THERAPY DATA MANAGEMENT SYSTEMS, DEVICES, AND METHODS," both of which are incorporated by reference herein in their entireties.

TECHNICAL FIELD

The present technology generally relates to systems and methods for collecting, storing, monitoring, reporting, and/or analyzing patient treatment data associated with patient usage of one or more respiratory therapy devices.

BACKGROUND

Respiratory therapies such as mechanical ventilation, supplemental oxygen, and the like are administered to patients in a variety of settings. For example, patients may receive respiratory therapies in intensive care units, emergency rooms, clinics, long-term care facilities, rehabilitation facilities, or at home. It is often not practical or even possible for a healthcare provider to be in physical proximity to the patient at all times and in all settings to monitor the patient's respiratory therapies. Accordingly, a need exists for systems that can monitor, record, analyze, and/or report patient treatment data associated with patient usage of respiratory therapy devices.

BRIEF DESCRIPTION OF THE DRAWINGS

Many aspects of the present technology can be better understood with reference to the following drawings. The components in the drawings are not necessarily to scale. Instead, emphasis is placed on clearly illustrating the principles of the present technology.

FIG. 7 illustrates an example therapy log report displaying simulated patient therapy data and generated in accordance with select embodiments of the present technology.

DETAILED DESCRIPTION

Figure 1A:
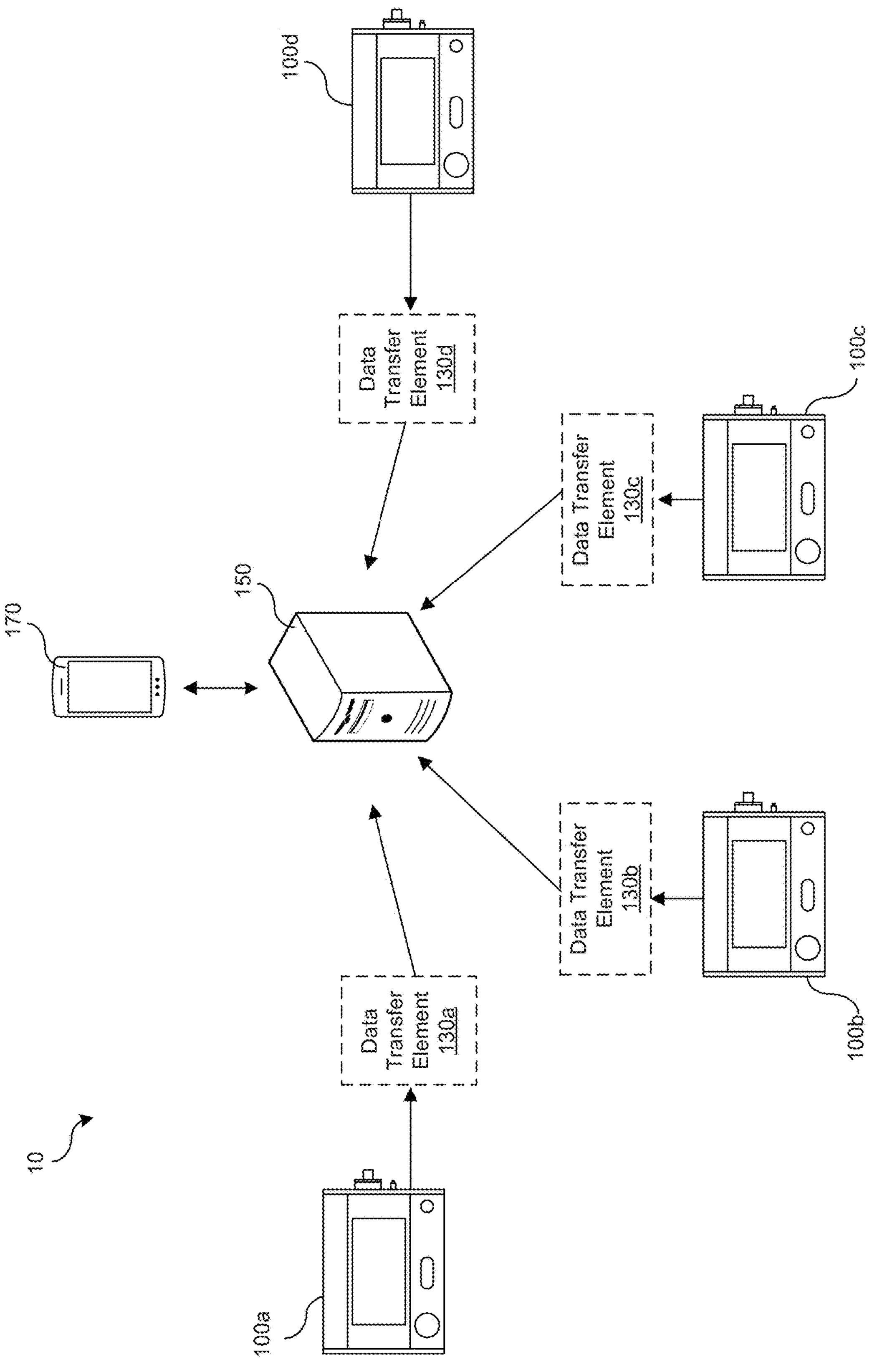
FIGS. 1A and 1B are schematic illustrations of a respiratory therapy data management system configured in accordance with select embodiments of the present technology.

The present technology is directed to respiratory therapy data management systems, device, and methods. The systems described herein can collect, store, monitor, report, and/or analyze patient treatment data associated with patient use of one or more respiratory therapy devices. The patient treatment data can include therapy data related to the use of multiple respiratory therapies, such as ventilation, oxygen, cough-assistance, suction, and nebulization. The patient treatment data may be collected from a plurality of respiratory devices associated with a particular patient, or from a single respiratory device associated with a particular patient. The system can generate customizable therapy reports and/or summaries detailing the patient treatment data. The patient therapy reports can summarize patient use of the various respiratory therapies, illustrate therapy trends, and/or provide therapy recommendations. Without being bound by theory, the systems described herein are therefore able to facilitate informed treatment decisions, promote proactive clinical interventions, control costs, and help coordinate care across multiple healthcare providers.

In a representative embodiment, the present technology provides a method for monitoring treatment of a patient. The method can include collecting patient treatment data associated with a plurality of respiratory therapies used by the patient. The plurality of respiratory therapies can include, for example, ventilation therapy, oxygen therapy, cough-assistance therapy, suction therapy, and/or nebulization therapy. The method can further include transmitting the collected patient treatment data to a server, which includes a patient data module storing data associated with a plurality of individual patients. The method can further include generating and displaying a patient therapy report summarizing the patient's use of the various respiratory therapies, illustrating therapy trends, and/or providing therapy recommendations for improving the quality of life of the patient.

Further aspects and advantages of the devices, methods, and uses will become apparent from the ensuing description that is given by way of example only.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1A-8.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, “generally,” “approximately,” and “about” are used herein to mean the stated value plus or minus 10%. The term “substantially” or grammatical variations thereof refers to at least about 50%, for example, 75%, 85%, 95%, or 98%.

FIG. 1A is a schematic illustration of a respiratory therapy data management system 10 (the “system 10”) configured in accordance with select embodiments of the present technology. The system 10 includes a plurality of ventilators 100*a-d* and a server 150. The ventilators 100*a-d* can be configured to provide ventilation and/or other respiratory therapy to patients in need thereof. The ventilators 100*a-d* can be the same model or different models, and can be manufactured by the same entity or by different entities. Each ventilator 100*a-d* can be associated with a particular individual patient. For example, the first ventilator 100*a* may be associated with a first particular patient, the second ventilator 100*b* may be associated with a second particular patient, the third ventilator 100*c* may be associated with a third particular patient, and the fourth ventilator 100*d* may be associated with a fourth particular patient. In some embodiments, more than one ventilator is associated with a particular patient. For example, the first ventilator 100*a* and the second ventilator 100*b* may both be associated with the same particular patient. Furthermore, although shown as ventilators for providing mechanical breath assistance, the system 10 may include other respiratory therapy devices in addition to, or in lieu of, the ventilators 100*a-d.* For example, the system 10 may include oxygen concentrators, cough-assist devices, drug infusion pumps, or the like.

The server 150 can be a local server or a remote server, and can include one or more computing devices and/or systems. As discussed further herein, the server 150 can include one or more processors, and memory storing instructions executable by the one or more processors to perform the methods described herein. In some embodiments, the server 150 is implemented as a distributed “cloud” computing system or facility across any suitable combination of hardware and/or virtual computing resources.

As described in greater detail with reference to FIG. 2, the ventilators 110*a-d* are configured to transmit patient treatment data collected and/or generated by the ventilators 100*a-d* to the server 150 for collection, storage, reporting, analysis, or the like. The transmitted patient treatment data can include patient data, ventilator data, therapy data, or the like. Patient data can include data associated with a particular patient with which the corresponding ventilator is associated, such as a patient identifier, age, height, weight, sex, medical history, diagnosis, test results, condition, therapy prescription, therapy recommendation, prognosis, or the like. Ventilator data can include data associated with the ventilator, such as manufacturer, make, model, serial number, parts list, features list, location (e.g., GPS location of the ventilator), battery status, media bed status, environmental conditions, or the like. Therapy data can include usage data, recorded or measured parameters, alarm data, event data, diagnostic data, or the like. Additional details of the patient treatment data transmitted to the server 150 are described below with respect to FIG. 2.

In some embodiments, the ventilators 100*a-d* include corresponding data transfer elements 130*a-d* for collecting patient treatment data from the ventilators 100*a-d* and/or for transferring the patient treatment data from the ventilators 100*a-d* to the server 150. As described in greater detail with reference to FIG. 2, the data transfer elements 130*a*-130*d* can establish a wired or wireless connection with the ventilators 100*a*-100*d* and the server 150, and can therefore be used to securely transmit data from the ventilators 100*a*-100*d* to the server 150.

The system 10 can further optionally include one or more computing devices 170. The computing devices 170 can be used to access the server 150 for downloading, reviewing, and/or analyzing data stored on the server 150. The computing device 170 can be any suitable user device, such as a smart phone, mobile device, laptop, desktop, personal computer, tablet, or other such devices known in the art. As discussed in greater detail with reference to FIG. 2, the computing device 170 can include a communication module for communicating with the server 150 and a display for displaying data to a user. In some embodiments, the computing device 170 can be associated with a healthcare provider that is treating the patient. In some embodiments, the computing device 170 can be associated with a patient receiving respiratory therapy from one of the ventilators 100*a-d,* and/or a caregiver for the patient receiving respiratory therapy.

As one skilled in the art will appreciate, the system 10 can include any number of ventilators 100. For example, the system 10 can have as few as a single ventilator in some embodiments (e.g., if the server is a local server dedicated to a single patient). In other embodiments, the system may include ten or more, 50 or more, 100 or more, 500 or more, or 1,000 or more ventilators or other respiratory devices (e.g., if the server is a remote server receiving data for many different patients). Accordingly, in some embodiments the system 10 can be configured to collect, store, monitor, report, and/or analyze patient treatment data for a plurality of patients (e.g., ten or more, 50 or more, 100 or more, 500 or more, 1,000 or more, etc.).

Figure 1B:
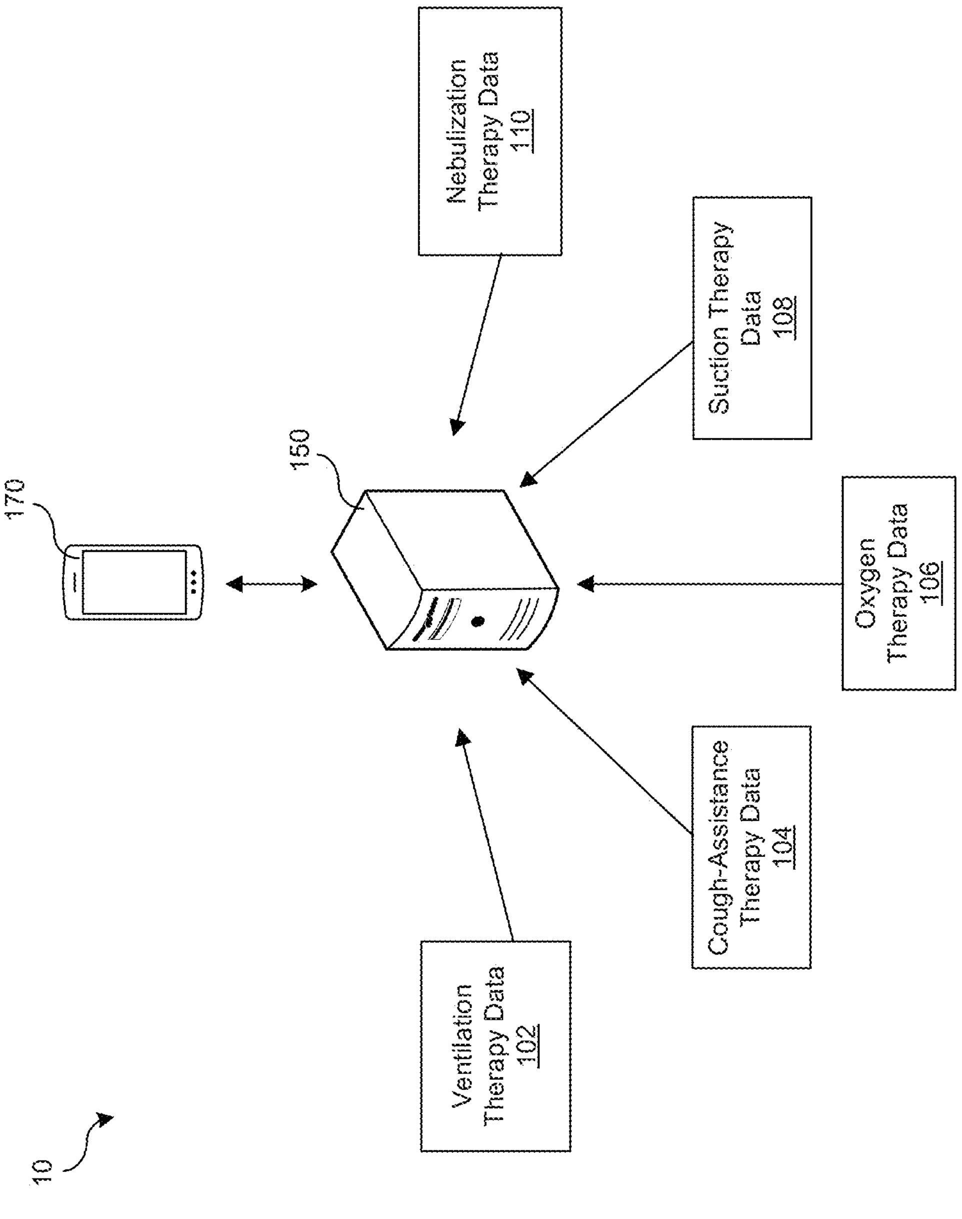

FIG. 1B illustrates additional aspects of the system 10. For example, the server 150 can be configured to receive a plurality of therapy data, including ventilation therapy data 102, cough-assistance therapy data 104, oxygen therapy data 106, suction therapy data 108, and/or nebulization therapy data 110. The therapy data can be associated with a single patient or multiple patients. Additionally, if the therapy data is associated with a single patient, the data can be received from the same or different devices (and/or from one or more data transfer elements 130). For example, in some embodiments the therapy data is received from a single respiratory device that incorporates each of the five therapies (e.g., the ventilator 200 described with respect to FIG. 2). In other embodiments, the therapy data is received from multiple individual devices (e.g., the ventilation therapy data 102 is received from a ventilator, the cough-assistance therapy data 104 is received from a cough-assist device, the oxygen therapy data 106 is received from an oxygen concentrator, etc.). Additional details of the therapy data are described below with respect to FIG. 2. Further, as also described in detail below, the server 150 can generate a single, comprehensive patient therapy report that includes some or all of the received therapy data. The patient therapy report can be transmitted to the computing device 170 for display to a user.

Figure 2:
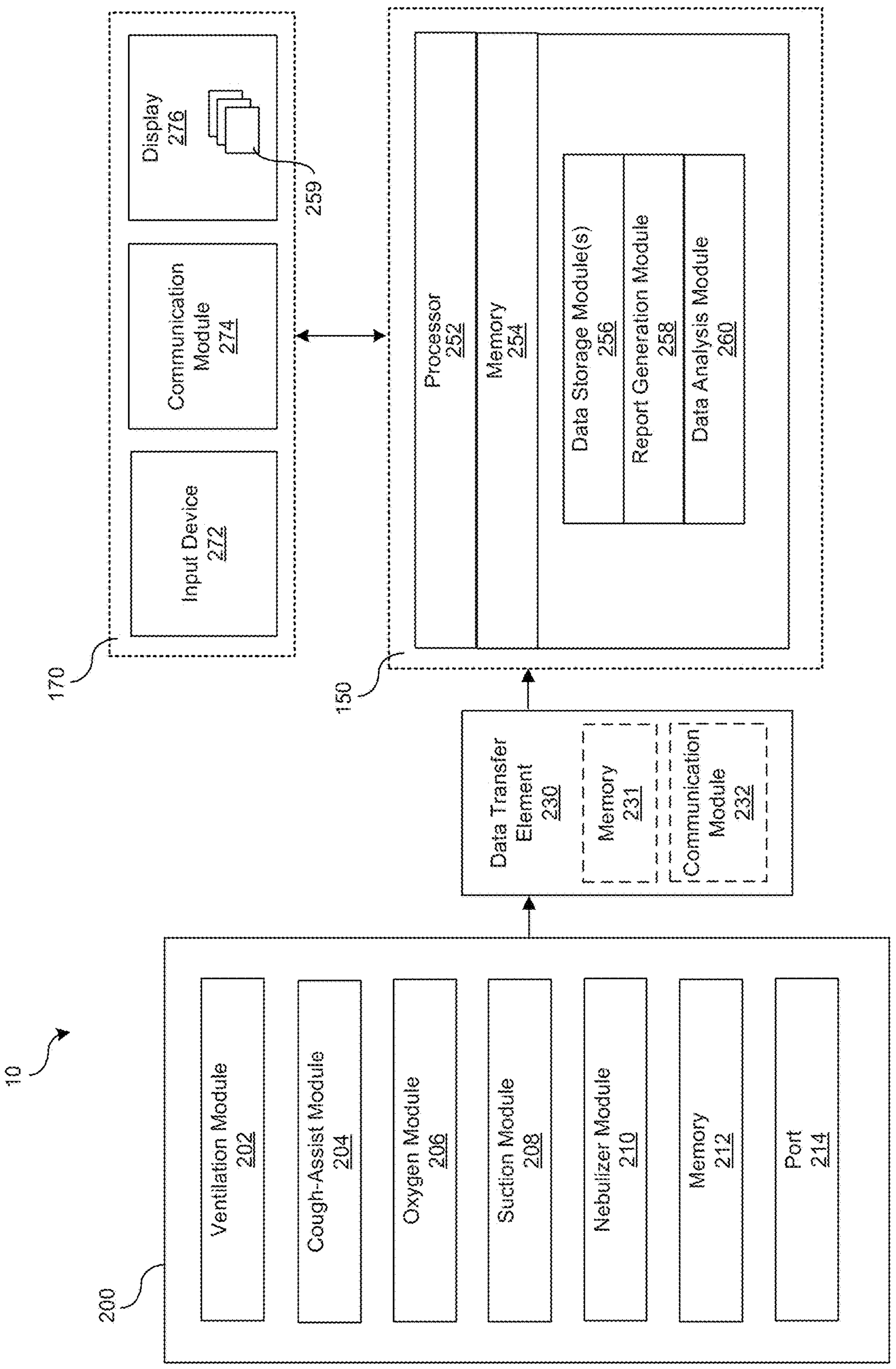
FIG. 2 is a schematic illustration of select features of the respiratory therapy data management system shown in FIGS. 1A and 1B.

FIG. 2 is a schematic illustration of the system 10 shown in FIGS. 1A and 1B and illustrates additional features of a ventilator 200 (which can be one of the ventilators 100*a-d* or a separate ventilator also included in the system 10), a data transfer element 230 (which can be one of the data transfer elements 130_a-d_ or a separate data transfer element also included in the system 10), the server 150, and the computing device 170.

As provided above, the ventilator 200 is configured to provide respiratory therapy to a patient in need thereof. The ventilator 200 can include a plurality of therapy modules for delivering different therapies to a patient. For example, in the illustrated embodiment the ventilator 200 includes a ventilation module 202 for providing breathing therapy to the patient, a cough-assist module 204 for providing cough-assistance to the patient, an oxygen module 206 for providing oxygen therapy to the patient, a suction module 208 for providing suction to the patient, and a nebulizer module 210 for delivering a therapeutic agent to the patient. The ventilator 200 can include additional or fewer therapy modules than illustrated in FIG. 2. For example, the ventilator 200 can include any combination of the five therapy modules illustrated in FIG. 2, and/or additional therapy modules not expressly described herein.

The ventilator 200 may further include a memory 212. The memory 212 can record and store patient treatment data. For example, the memory 212 may store patient-preferred ventilator settings/parameters, patient usage of the various therapy modules, and the like. The ventilator 200 may further include a port 214 for receiving or otherwise interfacing with a data transfer element, such as the data transfer element 230. As one skilled in the art will appreciate, the ventilator 200 may have additional features not expressly described herein, such as any of those described in U.S. Pat. Nos. 9,956,371, 10,046,132, 10,105,509, 10,245,406, 10,315,002, 10,518,059, 10,758,699, and 10,773,049, the disclosures of which are incorporated by reference herein in their entireties and for all purposes.

The ventilator 200 can be operably coupled to the data transfer element 230. The data transfer element 230 can be a bridge or other transmitter configured to transmit data from the ventilator 200 to the server 150, as described below. In some embodiments, the data transfer element 230 is removably couplable to the ventilator 200 (e.g., via the port 214). In other embodiments, the data transfer element 230 is integrated into the ventilator 200 itself. In some embodiments, the data transfer element 230 is wirelessly couplable to the ventilator 200. Regardless, the data transfer element 230 can continuously or semi-continuously interface with the ventilator 200 over a period of time to record, store, monitor, and transmit patient treatment data from the ventilator 200 to the server 150. In some embodiments, the data transfer element 230 may include a memory 231 for storing patient treatment data. In such embodiments, the memory 231 may store the patient treatment data in addition to, or in lieu of, the memory 212 of the ventilator 200 storing the patient treatment data.

In some embodiments, the data transfer element 230 can record, collect, and/or monitor patient treatment data associated with other medical devices in addition to the ventilator 200. For example, the data transfer element 230 can also be connected (e.g., physically or wirelessly, e.g., via Bluetooth) to a blood pressure monitor for measuring patient blood pressure, a blood glucose monitor for measuring patient blood glucose, a heart rate monitor for measuring patient heart rate, an $SpO_2$ monitor (e.g., a pulse oximeter) for measuring oxygen saturation, a carbon dioxide monitor for measuring exhaled carbon dioxide ($ECO_2$), a scale for monitoring patient weight, a drug delivery device (e.g., an infusion pump, an inhaler, etc.) for administering a therapeutic agent, an activity monitor for monitoring patient activity, a smart watch, or the like. In some embodiments, the data transfer element 230 can be simultaneously connected to both the ventilator 200 and one or more additional medical devices. Accordingly, the data transfer element 230 can collect patient treatment data across multiple medical devices associated with the treatment of a particular patient. As described in detail below, the collected patient treatment data for these multiple devices can be compiled into a single patient treatment report for ease of viewing. As also described in detail below, and without being bound by theory, collecting patient data from multiple devices and/or for multiple therapies is expected to improve treatment of patients by enabling a healthcare provider to have a more comprehensive review of the patient's therapy and associated symptoms, as opposed to reviewing each therapy-type in isolation.

In some embodiments, the data transfer element 230 can wirelessly transmit the patient treatment data to the server 150. For example, the data transfer element 230 can include a communication module 232 for establishing a wireless connection with the server 150. The communication module 232 can be configured to connect the data transfer element 230 to the server 150 using cellular, WIFI, Bluetooth, RF communication, Near-Field-Communication, or other suitable wireless communication technique(s). In some embodiments, the data transfer element 230 can be physically connected to the server 150 to transfer the patient treatment data thereto. For example, the data transfer element 230 can be a USB drive or other physical device having memory and that can be plugged into the server 150 (or the computing device 170) to transfer the patient treatment data thereto. Although described as sending data directly to the server 150, in some embodiments the data transfer element 230 may send data to one or more intermediate devices (e.g., computing device 170), and the one or more intermediate devices can send the data to the server 150. In such embodiments, the data transfer element 230 may send the data to the one or more intermediate devices via a physical connection mechanism or via any of the previously described wireless communication networks. The data transfer element 230 can be configured to transmit data to the server 150 continuously, periodically (e.g., twice-per-day, once-per-day, twice-per-week, once-per-week, twice-per-month, once-per-month, etc.) and/or on demand (e.g., a patient or healthcare provider selects an "upload data" option on a controller interface (not shown) on the ventilator 200 and/or the computing device 170).

In some embodiments, the server 150 is configured to receive patient treatment data from a plurality of sources. For example, in embodiments in which the server 150 receives and stores patient treatment data from a plurality of ventilators, some ventilators may directly transmit the patient treatment data to the server 150 via the data transfer element 230, while other ventilators may upload patient treatment data to a secondary server or cloud platform, and the server 150 can then retrieve the uploaded patient treatment data from the secondary server or cloud platform. Enabling the server 150 to receive patient treatment data from different sources is expected to enable the system 10 to collect and store patient treatment data for many different medical devices, e.g., even if the medical devices have their own data collection or communication systems. For example, as previously described, the system 10 can collect and store data associated with a large number of ventilators, even if the ventilators have different manufacturers and/or collect and transmit data in different manners. Without being bound by theory, the system 10 therefore can provide a central, consolidated database of patient treatment data, regardless of the manufacturer of the medical devices that the patient treatment data is being collected from.

The patient treatment data collected and stored by the ventilator 200 and/or the data transfer element 230 (and transmitted to the server 150) can include patient data, ventilator data, and/or therapy data. The patient data can include a patient identifier (e.g., a unique alpha-numeric code that is HIPAA compliant for use with Electronic Medical Records), age, height, weight, sex, diagnosis, test results, condition, medical history, or the like. The ventilator data can include manufacturer, make, model, serial number, parts list, features list, location (e.g., GPS location of the ventilator), battery status, media bed status, environmental conditions, or the like. As described in more detail below, the therapy data can include usage data (e.g., usage data associated with various therapy modules), trend data, event data, alarm data, compliance data, diagnostic data, or the like.

In some embodiments, the therapy data can include ventilation therapy data (e.g., ventilation therapy data 102; FIG. 1B), which can include usage data associated with the ventilation module 202. For example, the usage data can include the hours per day the ventilation module 202 was used by the patient during a select time period, the number of days the ventilation module 202 was used by the patient in a select time period, and/or other data associated with the usage of the ventilation module 202. The ventilation therapy data can also include additional data associated with the patient use of the ventilation module 202, including, but not limited to, data (e.g., measured or calculated parameters) associated with exhaled tidal volume (VTE), breath rate, minute volume, mean airway pressure (MAP), peak inspiratory pressure (PIP), positive end expiratory pressure (PEEP), expiratory positive airway pressure (EPAP), leak, patient triggering (e.g., percent of breaths triggered by the patient), inspiratory-expiratory (I:E) ratio, plateau pressure, static compliance, airway clearance, or the like. The ventilation therapy data can also include pressure waveforms, flow waveforms, and/or volume waveforms for the patient.

In some embodiments, the therapy data can further include cough-assistance therapy data (e.g., cough-assistance therapy data 104; FIG. 1B), which can include usage data associated with the cough-assist module 204. For example, the usage data can include the number of days the cough-assist module 204 was used by the patient in a select time period, the number of cough-assist maneuvers performed using the cough-assist module 204 in a select time period, the average daily number of cough-assist maneuvers performed using the cough-assist module 204 in a select time period, and/or other data associated with the usage of the cough-assist module 204. The cough-assistance therapy data can also include additional data associated with the patient use of the cough-assist module 204, including, but not limited to, data (e.g., measured or calculated parameters) associated with peak cough flow, cough volume, insufflation pressure, exsufflation pressure, insufflation time, exsufflation time, pause time, and/or insufflation rise time.

In some embodiments, the therapy data can further include oxygen therapy data (e.g., oxygen therapy data 106; FIG. 1B), which can include usage data associated with the oxygen module 206. For example, the usage data can include the hours per day the oxygen module 206 is used by the patient in a select time period, the number of days the oxygen module 206 was used by the patient in a select time period, and/or other data associated with the usage of the oxygen module 206. The oxygen therapy data can also include additional data associated with the patient use of the oxygen module 206, including, but not limited to, oxygen source (e.g., high pressure oxygen generator, low pressure oxygen generator, integrated oxygen generator, etc.), oxygen delivery mode (e.g., $FiO_2$, pulse dose, bleed in, etc.), oxygen flow equivalent, average $FiO_2$ percentage, low $FiO_2$ percentage, and/or high $FiO_2$ percentage.

In some embodiments, the therapy data can further include suction therapy data (e.g., suction therapy data 108; FIG. 1B), which can include usage data associated with the suction module 208. For example, the usage data can include the number of days the suction module 208 was used by the patient in a select time period, the number of suction sessions performed using the suction module 208 in a select time period, the average daily number of suction sessions performed using the suction module 208, the duration of individual suction sessions, the lowest number of suction session performed in a single day in a select time period, the highest number of nebulizer sessions performed in a single day in a select time period, and/or other data associated with the usage of the suction module 208. The suction therapy data can also include additional data associated with use of the suction module 208, including, but not limited to, data associated with vacuum pressure during the suction sessions.

In some embodiments, the therapy data can further include nebulization therapy data (e.g., nebulization therapy data 110; FIG. 1B), which can include usage data associated with the nebulizer module 210. For example, the usage data can include the number of days the nebulizer module 210 was used by the patient in a select time period, the number of nebulizer sessions performed using the nebulizer module 210 in a select time period, the average daily number of nebulizer sessions performed using the nebulizer module 210 in a select time period, the duration of individual nebulizer sessions, the lowest number of nebulizer sessions performed in a single day in a select time period, the highest number of nebulizer sessions performed in single day in a select time period, and/or other data associated with the usage of the nebulizer module 210. The nebulization therapy data can also include additional data associated with use of the nebulizer module 210, including, but not limited to, the type of therapeutic agent or drug administered, the dose of therapeutic agent delivered during each nebulizer session, the total dose of therapeutic agent administered over the entirety of the given time period, and/or the average daily dose of the therapeutic agent administered.

Any of the foregoing parameters can be measured, determined, collected, stored, and/or reported as continuous values (e.g., shown on a line graph), periodic values (e.g., values taken once per second, once every 5 seconds, once every 10 seconds, once every 15 seconds, once every 30 seconds, once per minute, once every two minutes, once every five minutes, once ever ten minutes, etc.), and/or average values (e.g., hourly averages, daily averages, weekly averages, etc.). As one skilled in the art will appreciate, the therapy data can include additional data associated with the patient use of the ventilator 200 not expressly described herein. The foregoing parameters are provided merely as examples and in no way limit the scope of the present disclosure.

As shown in FIG. 2, the server 150 includes a processor 252 and a memory 254. The memory 254 stores one or more software modules for performing one or more steps of the methods described herein. For example, the memory 254 can store a data storage module 256, a report generation module 258, and a data analysis module 260. In alternative embodiments, one or more of these modules may be combined with each other, or may be omitted. Thus, although certain operations are described herein with respect to a particular module or modules, this is not intended to be limiting, and such operations can be performed by a different module or modules in alternative embodiments.

The data storage module 256 can receive and store the patient treatment data. For example, the data storage module 256 can receive the patient treatment data from the ventilator 200 via the data transfer element 230. The data storage module 256 can also store past patient treatment data associated with a particular patient, so that received patient treatment data can be compared to past patient treatment data for the same patient. The data storage module 256 can therefore generate and maintain a plurality of patient profiles, with each patient profile corresponding to a particular patient. The patient profiles can be anonymized or otherwise encrypted to comply with HIPAA and privacy requirements.

The report generation module 258 can generate patient reports or summaries of the therapy data received and/or stored in the data storage module 256. For example, the report generation module 258 can prepare reports/summaries for a particular patient in response to a user request. The report generation module 258 can therefore interact with the data storage module 256 to identify and retrieve patient treatment data therefrom. The report generation module 258 can then generate a patient therapy report based on the retrieved patient treatment data, and the server 150 can transmit the generated patient therapy report to the computing device 170 for display to the user. Although described as generating a "report," in some embodiments a user is able to access the data storage module 256 directly (e.g., via the computing device 170) to directly review, sort, or analyze data stored therein.

In some embodiments, the patient therapy report or summary includes therapy data for a plurality of respiratory and/or non-respiratory therapies. For example, the patient therapy report can include therapy data for respiratory therapies such as ventilation therapy, cough therapy, oxygen therapy, suction therapy, and/or nebulization therapy. In addition, the patient therapy report can also include data for non-respiratory therapies, such as diabetes therapies or the like. The patient therapy report can further include therapy data collected from other medical devices monitoring various physiologic parameters of the patient, such as a heart rate monitor, a blood pressure monitor, a blood glucose monitor, an $SpO_2$ monitor, a carbon dioxide monitor, a scale, a drug delivery device, an activity monitor, a smart watch, or the like. Accordingly, the patient therapy report can provide a comprehensive or holistic overview of the patient's treatment, response to treatment, symptoms, and the like. Without being bound by theory, providing a comprehensive patient therapy report is expected to enable healthcare provides to better extract patient trends and interactions between various therapy types. As a non-limiting example, if the patient therapy report includes ventilation therapy data, cough therapy data, and suction therapy data, a healthcare provider can review the cough therapy data and suction therapy data to examine how the patient's use of cough therapy and suction therapy affects the patient's ventilation. As another non-limiting example, if the patient therapy report includes ventilation therapy data (e.g., from a ventilator), blood pressure measurements (e.g., from a blood pressure monitor), and heart rate measurements (e.g., from a heart rate monitor), a healthcare provider can review the ventilation therapy data to examine how different ventilation therapy modes or operating parameters affect the patient's blood pressure and heart rate. Without being bound by theory, providing a consolidated and comprehensive report is therefore expected to improve patient treatment outcomes by enabling healthcare providers to simultaneously review data across multiple therapy modalities and therefore "fine-tune" therapy to optimize patient outcomes.

As set forth above, the patient therapy data stored on the server 150 can include ventilation therapy data including pressure waveforms, flow waveforms, and/or volume waveforms (collectively referred to as "waveform data"). In some embodiments, the generated patient therapy reports or summaries can therefore include waveform data, enabling a healthcare provider to remotely monitor and/or review these waveforms. In some embodiments, the server 150 can store historical waveform data for a patient for the previous 30 days, 60 days, 90 days, etc., and a healthcare provider can review waveform data for any time period within the stored period. In some embodiments, and as described in more detail below, the system 10 enables the healthcare provider to review the waveform data in substantially real-time.

In some embodiments, the data analysis module 260 can also analyze the patient treatment data stored in the data storage module 256. For example, the data analysis module 260 may analyze the patient treatment data to review patient compliance with a prescribed and/or recommended therapy regimen. As a first non-limiting example, the data analysis module 260 can compare whether the number or rate of cough-assist maneuvers performed over a select time period is the same as a prescribed or recommended number of cough-assist maneuvers to be performed over the given time period. If the number or rate of cough-assist maneuvers performed over the given time period is less than the prescribed or recommended amount, the data analysis module 260 can direct the server 150 to (i) send the patient a reminder to increase their use of the cough-assist module 204, (ii) send the patient's healthcare provider a notice that the patient is not complying with the prescribed or recommended therapy regimen, and/or (iii) include a notice that the patient is not complying with the prescribed or recommended therapy regimen on a patient therapy report generated by the report generation module 258. As a second non-limiting example, the data analysis module 260 can determine whether a patient is receiving a prescribed dosage of a therapeutic agent by analyzing the therapy data associated with the nebulizer module 210. If the received dosage is not within a threshold degree of deviation of the prescribed dosage (e.g., within 5% of the prescribed dose, within 10% of the prescribed dose, etc.), the data analysis module 260 can direct the server 150 to (i) send the patient instructions for changing their use of the nebulizer module 210 so that they receive the prescribed dosage, (ii) send the patient's healthcare provider a notice that the patient is not receiving the prescribed dosage, and/or (iii) include a notice that the patient is not receiving the prescribed dosage on a patient therapy report generated by the report generation module 258. As one skilled in the art will appreciate, the data analysis module 260 can analyze patient compliance with any number of prescribed, recommended, or preferred therapy regimens, and is not limited by the foregoing examples.

The data analysis module 260 can also analyze the patient treatment data to distil patient trends, diagnose patient conditions/events, provide therapy recommendations, predict disease progression, or the like. For example, the data analysis module 260 can analyze usage data over a prolonged period of time (e.g., three months, six months, nine months, one year, two years, three years, five years, ten years, or more) to assess patient dependence on the various therapy functions and/or disease progression. In some embodiments, increased patient dependence on select ventilator functions (e.g., time spent relying on the ventilation module 202 to provide a breath, reliance on the oxygen module 204 to provide additional oxygen, etc.) may indicate disease progression and/or declining patient condition. Likewise, a change in one or more parameters associated with patient usage of the ventilator functions (e.g., percentage of breaths triggered by the patient) may also indicate disease progression and/or declining patient condition.

The data analysis module 260 can also compare therapy data for a particular patient with aggregated therapy data for a plurality of other patients who share one or more common characteristics with the patient (e.g., age, sex, weight, height, diagnosis, age of diagnosis, condition, disease state, test results, activity level, etc.). Based on the comparison, the data analysis module 260 can provide one or more therapy recommendations to slow disease progression, reduce patient symptoms, reduce or eliminate side effects, improve patient quality of life, or the like. The data analysis module 260 may also provide an estimate of disease progression based on the comparison.

The data analysis module 260 may rely on one or more artificial intelligence (AI) techniques for analyzing patient treatment data and providing recommendations. Suitable AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems. In some embodiments, for example, the data analysis module 260 includes a trained machine learning module that can analyze patient treatment data for a particular patient to provide one or more recommended adjustments to the patient's therapy regime to slow disease progression, reduce patient symptoms, reduce or eliminate side effects, improve patient quality of life, or the like. The machine learning module can be trained based on, for example, previously received patient treatment data sets that include scored outcomes corresponding to patient symptoms, side effects, quality of life, disease progression, etc.

As provided above, the system 10 can further include a computing device 170. The computing device 170 can include an input device 272, a communication module 274, and a display 276. The input device 272 can be any suitable input device, such as a mouse, a keyboard, a touchscreen, a touchpad, a microphone, or other user input device. The communication module 274 can be configured to establish a wireless connection with the server 150 using any suitable wireless communication technique (e.g., WIFI, Bluetooth, cellular, etc.). The display 276 can be configured to display various types of outputs, such as patient therapy reports generated by the report generation module 258 and described in detail below. In some embodiments, the display 276 includes the input device as part of the display 276, such as when the input device includes a touchscreen. In other embodiments, the display 276 is separate from the input device. Examples of suitable displays 276 include, but are not limited to, an LCD display screen, an LED display screen, or the like.

In operation, a user (e.g., a healthcare provider, the patient, the patient's caregiver, or other user) can request, via the input device 272 on the computing device 270, a patient therapy report for a particular patient. For example, a user may access a website, intranet, mobile phone application, or other application via the computing device 270 and input patient identification information (e.g., the patient's unique alpha-numeric identifier, the patient's name, the patient's unique log-in information, etc.). In some embodiments, the user can customize the report. For example, the user can specify the time period for which they would like to see patient treatment data, which medical devices (if more than one, e.g., a ventilator, a cough-assist device, a heart rate monitor, an infusion pump, etc.) the user would like to see data from, what patient data the user would like the report to include (e.g., usage data, specific events of interest, etc.), and/or the type of report to be generated (e.g., interactive, digital, print, etc.). In embodiments in which the patient also receives non-respiratory therapies (e.g., treatment for diabetes, etc.), the user can select to include data associated with the non-respiratory therapies (e.g., diabetes treatment data, etc.) such that the report is a single comprehensive report of the patient's health. Accordingly, in some embodiments the patient therapy reports are customized and/or customizable according to the user's preferences. In some embodiments, the patient therapy report may take different forms depending on whether the patient therapy report was requested by the patient or the healthcare provider. The computing device 170 then communicates the user's request to the server 150 via the communication module 274. In response to the receiving the user request, the report generation module 258 identifies and retrieves the requested patient treatment data from the data storage module 256 and generates a patient therapy report in accordance with the user's preferences. The server 150 transmits the patient therapy report to the computing device 170, where the report can be shown to the user via the display 276 (e.g., shown schematically as patient therapy report 259 in FIG. 2).

In some embodiments, the patient therapy reports generated by the report generation module 258 and displayed by the computing device 170 can be interactive. For example, a user can select or deselect certain parameters or values, select specific date ranges for display, toggle between different pages showing different parameters, adjust a graphical display of patient treatment data (e.g., adjust a scale, a graph type, etc.), select or mark particular events, add notes to the report (e.g., annotations, reminders, suggestions, etc.), or the like. In some embodiments, selecting a particular event (e.g., a patient-marked event) causes the report to display the related therapy data associated with the event (e.g., ventilation therapy data such as pressure, flow, and volume waveforms) during, before, and/or after the event. In some embodiments, a patient can add comments or questions to the report, or otherwise mark specific portions of the report, they would like to discuss with their healthcare provider. For example, the patient may add a comment or otherwise mark an event or time period during which they were feeling worse than normal. The report can then be transmitted to the patient's healthcare provider, who can see the comments, questions, and other markings on the report in addition to the corresponding patient treatment data. Likewise, a healthcare provider can add comments or notes to the report before sending it to the patient, the patient's caregiver, or another physician. Additional details of example patient therapy reports are described below with respect to FIGS. 3-7.

In some embodiments, the system 10 can be used to remotely monitor a patient in substantially real-time in addition to, or in lieu of, reviewing historical patient treatment data. For example, the system 10 can enable a healthcare provider to monitor a patient receiving respiratory therapy in a non-clinical setting (e.g., at home) without having to be in physical proximity with the patient. For example, the data transfer element 230 can transmit patient treatment data to the server 150 in substantially real-time (e.g., a delay of about 10 seconds or less, about 30 seconds or less, about 60 seconds or less, etc.), and the server 150 can generate a patient therapy report using the received patient treatment data. The server 150 can transmit the patient therapy report to the computing device 270 for review by the healthcare provider, and/or provide alerts to the computing device 270 on an as needed basis (e.g., in response to detecting non-compliance with prescribed therapy). In some embodiments, the data transfer element 230 may directly transmit the patient respiratory data to the computing device 270 when operating in a "live monitoring" mode. Regardless, the delay between the ventilator 200 measuring the data and the computing device 270 displaying the data can be less than about 30 seconds, less than about 60 seconds, and/or less than about 120 seconds. Accordingly, in some embodiments the system 10 is adapted to "live-stream" patient treatment data to a healthcare provider in a remote setting.

In some embodiments, the "live-stream" of patient treatment data can occur on an as-needed basis. For example, rather than continuously streaming the patient treatment data to the server 150, a healthcare provider tasked with remotely monitoring a patient can request, using the computing device 170, real-time data for a particular patient. In response to the healthcare provider's request, the server 150 can pull real-time data from the data transfer element 230 associated with the particular patient, and display the real-time data without a substantial delay (e.g., a delay of about 10 seconds or less, about 30 seconds or less, about 60 seconds or less, etc.). This may be useful, for example, if the patient or caregiver reaches out to healthcare provider to discuss their current therapy, and the healthcare provider wants immediate access to current patient treatment data to be able to advise the patient on a proper course of action. Any of the patient treatment data described herein, including ventilator waveform data (e.g., pressure waveform, flow waveform, volume waveform) can be collected and reported in substantially real-time to facilitate remote monitoring of the patient.

The system 10 can also be integrated with existing hospital communication/monitoring systems to provide enhanced monitoring of patient status and recordation of patient care in a hospital or other clinical setting. For example, the system 10 can stream patient treatment data in substantially real-time to monitors in nurse stations, provide remote alarms, automatically feed patient treatment data electronically into the hospital's electronic health records system, or the like.

In some embodiments, the system 10 can therefore be used to monitor and/or conduct analytics for a plurality of patients. A healthcare provider, ventilator manufacturer, durable medical equipment (DME) company, or other user with authorized access may be able to access, review, and/or analyze patient treatment data stored on the system 10 for the plurality of patients. In some embodiments, for example, the user can sort the patients based on various patient or therapy factors, such as to identify which patients meet one or more predefined criteria selected by the user. Based on the selected criteria, the server 150 can sort, rank, or otherwise list the patients and cause the sorted list of patients to be displayed to the user, such as via the computing device 170. Depending on the user (e.g., if the user is a ventilator manufacturer rather than a healthcare provider), the patient therapy data may be sorted using a HIPAA compliant identifier to maintain patient privacy. Representative criteria that can be selected by the user may include, for example, non-compliance with prescribed therapy, detected leaks that exceed a predetermined threshold, oxygen consumption, number of alarms, etc.

In some embodiments, the system 10 can be used to monitor and/or conduct analytics for a plurality of ventilators. For example, an entity associated with the ventilators (e.g., the ventilator manufacturer, the DME company, etc.) may wish to access the patient treatment data stored on the server 150 to analyze utilization of their ventilators, compliance with prescribed or recommended therapy regimens, effectiveness of select therapies, accessories alerts, service alerts, locations of their ventilators, or the like. As described previously, the patient therapy data may be de-identified to comply with privacy and HIPAA requirements, while still enabling the manufacturer to review patient therapy data and distil useful trends regarding ventilator usage and status.

Figure 3:
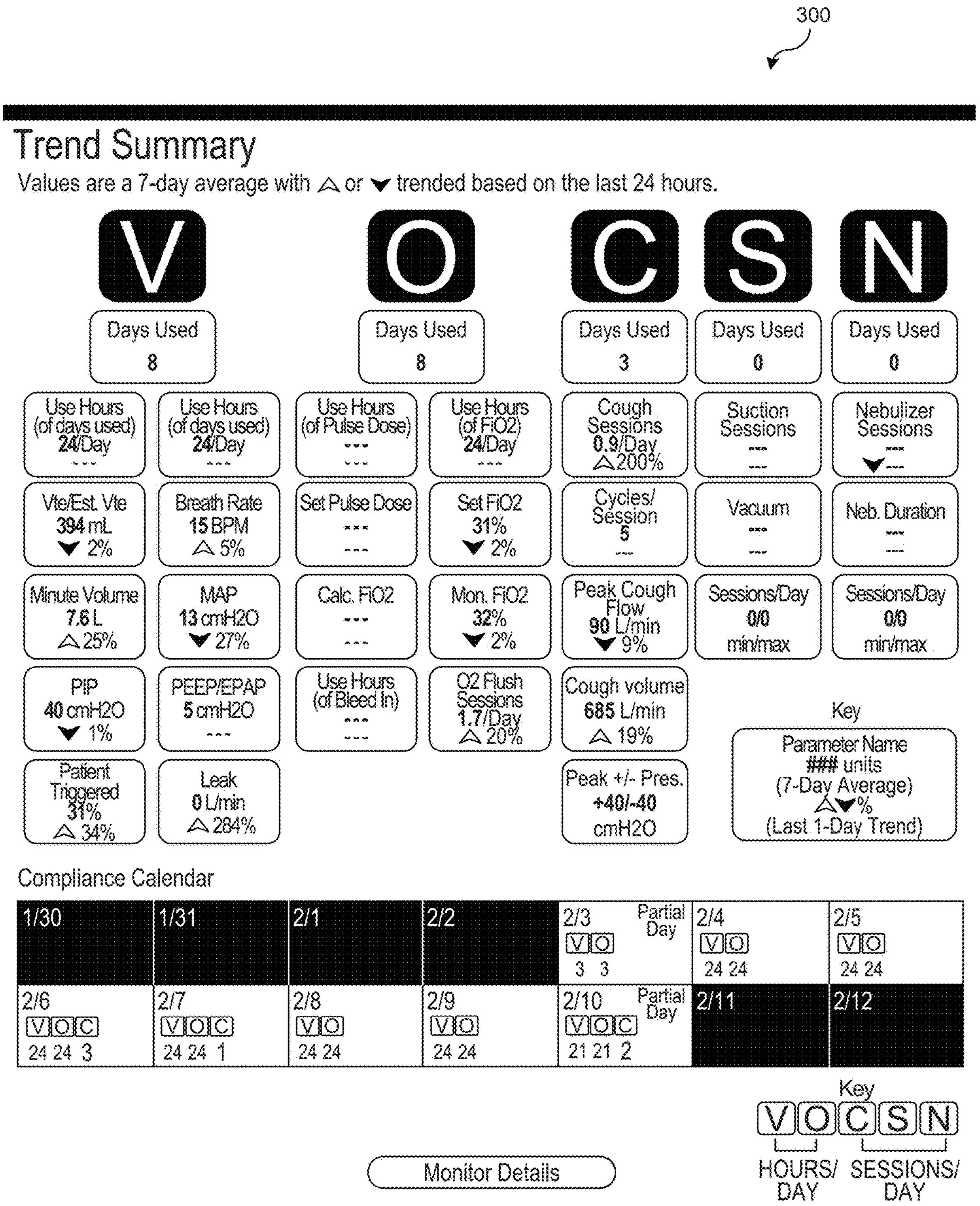
FIG. 3 illustrates an example trend summary report displaying simulated patient therapy data and generated in accordance with select embodiments of the present technology.

FIG. 3 illustrates an example trend summary 300 that can be included as part of a patient therapy report (e.g., the patient therapy report 259; FIG. 2) generated by the report generation module 258. The trend summary 300 can include a summary of therapy data for a particular patient, such as patient usage of select respiratory therapies (e.g., ventilation V, cough-assistance C, oxygen O, suction S, nebulization N, etc.) during a select time period, as well as other associated respiratory parameters. The trend summary 300 can also include a summary of non-respiratory therapies used by the patient (not shown in FIG. 3). The trend summary 300 can also include a compliance calendar illustrating the usage of various therapies by date.

Figure 4A:
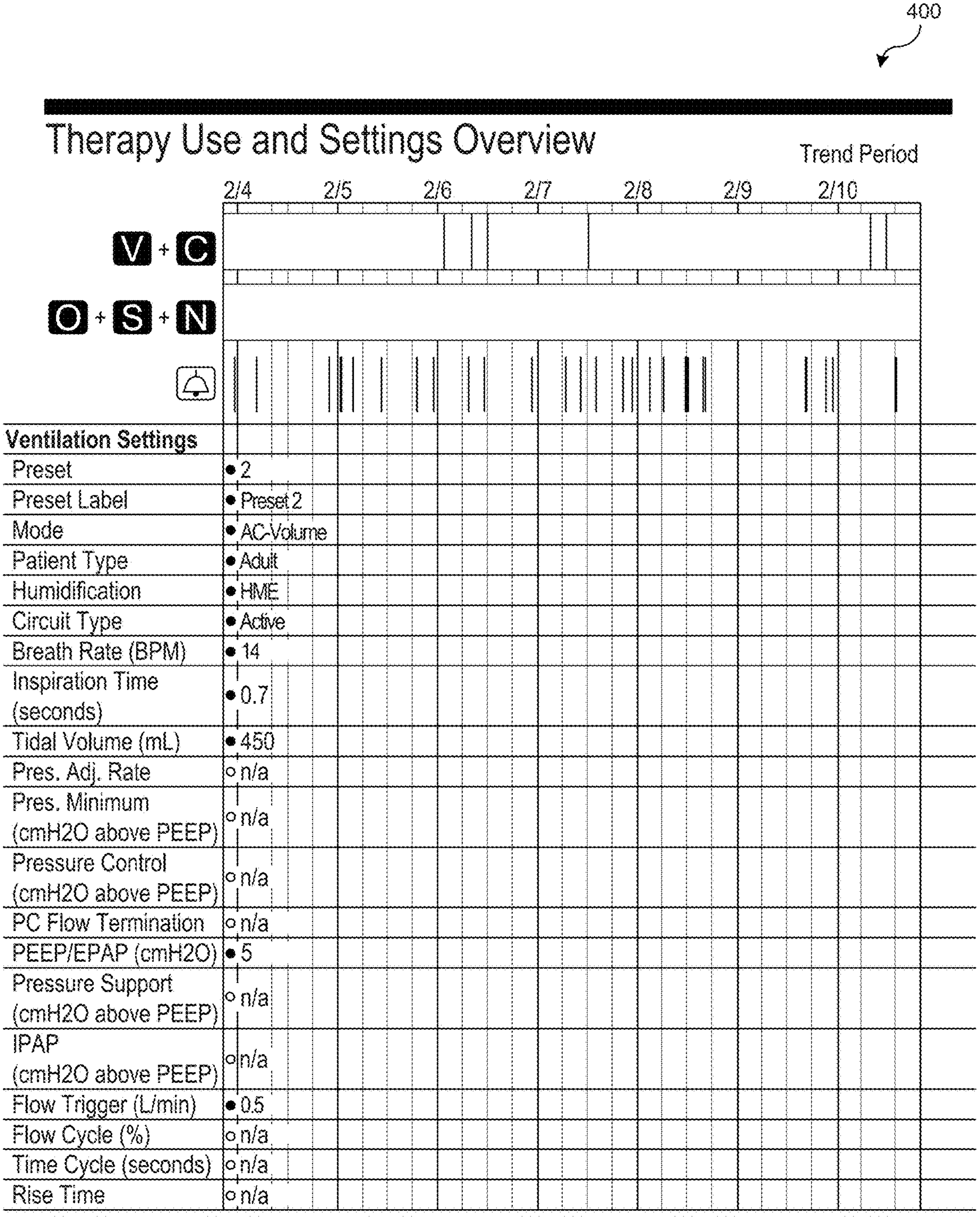
FIGS. 4A-4C illustrate an example therapy use and settings overview report displaying simulated patient therapy data and generated in accordance with select embodiments of the present technology.
Figure 4B:
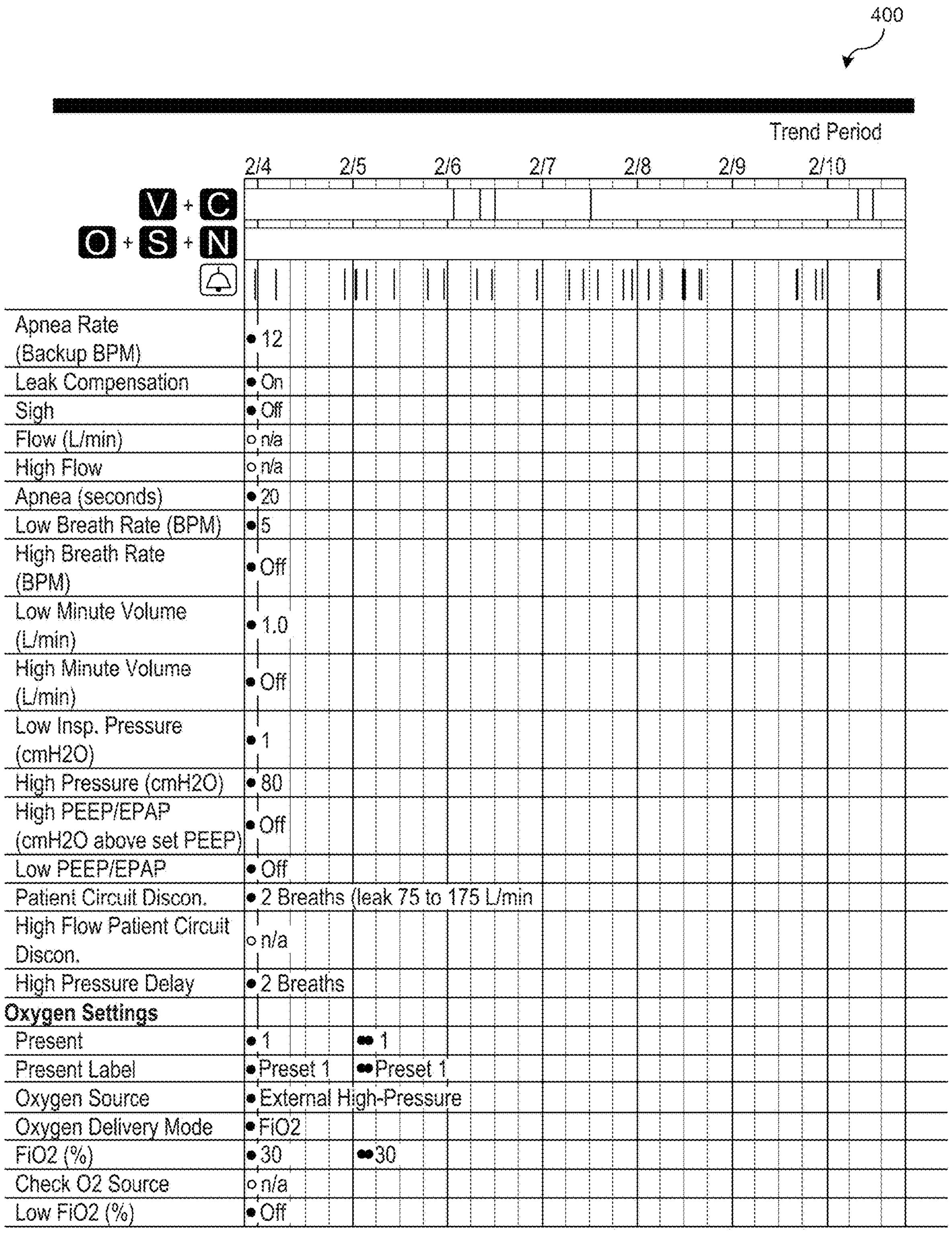
Figure 4C:
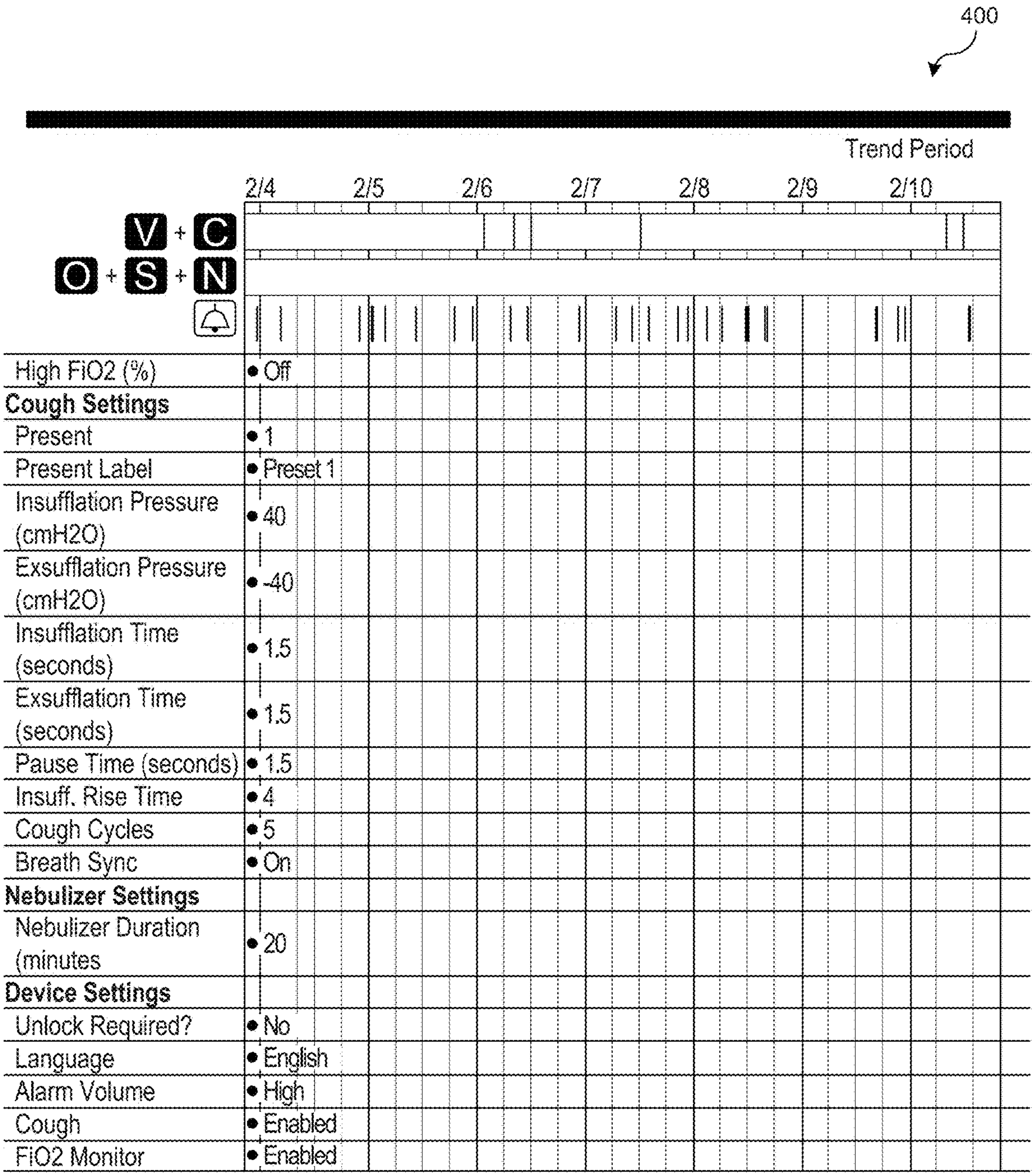

FIGS. 4A-4C illustrate an example therapy use and settings overview 400 that can be included as part of a patient therapy report (e.g., the patient therapy report 259; FIG. 2) generated by the report generation module 258. The therapy use and settings overview 400 can display use of, and parameters associated with the use of, the various respiratory therapies (e.g., ventilation, cough-assistance, oxygen, suction, nebulization, etc.) during a select time period. The therapy use and settings overview can also display use of, and parameters associated with, non-respiratory therapies used by the patient (not shown in FIGS. 4A-4C). In some embodiments, the therapy use and settings overview 400 includes the same or similar data as the trend summary 300. In some embodiments, the therapy use and settings overview 400 expands upon the data provided in the trend summary 300.

Figure 5:
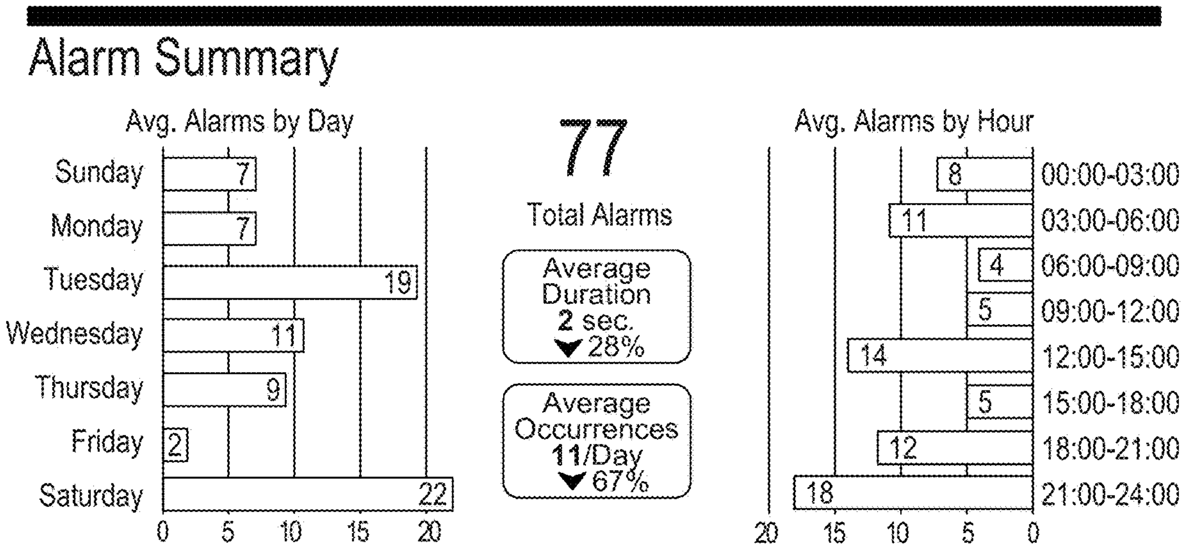
FIG. 5 illustrates an example alarm report displaying simulated patient therapy data and generated in accordance with select embodiments of the present technology.

FIG. 5 illustrates an example alarm summary 500*a*. The alarm summary 500*a* and the alarm log 500*b* can be included as part of a patient therapy report (e.g., the patient therapy report 259; FIG. 2) generated by the report generation module 258. As illustrated in FIG. 5, the alarm summary 500*a* can provide a summary of the frequency and type of alarms or alerts generated by a corresponding ventilator or other respiratory or medical device during a select time period. The alarms/alerts can include any alarm or alert provided by the ventilator or respiratory device. For example, the alarm may include a high-pressure alarm, a low inspiratory pressure alarm, a patient circuit disconnection alarm, a low minute volume alarm, a low battery alarm, etc. The alarm summary may also provide an alarm log (not shown) that provides a list of each individual alarm generated over a given time period, the timing of the alarm, and the duration of the alarm.

Figure 6A:
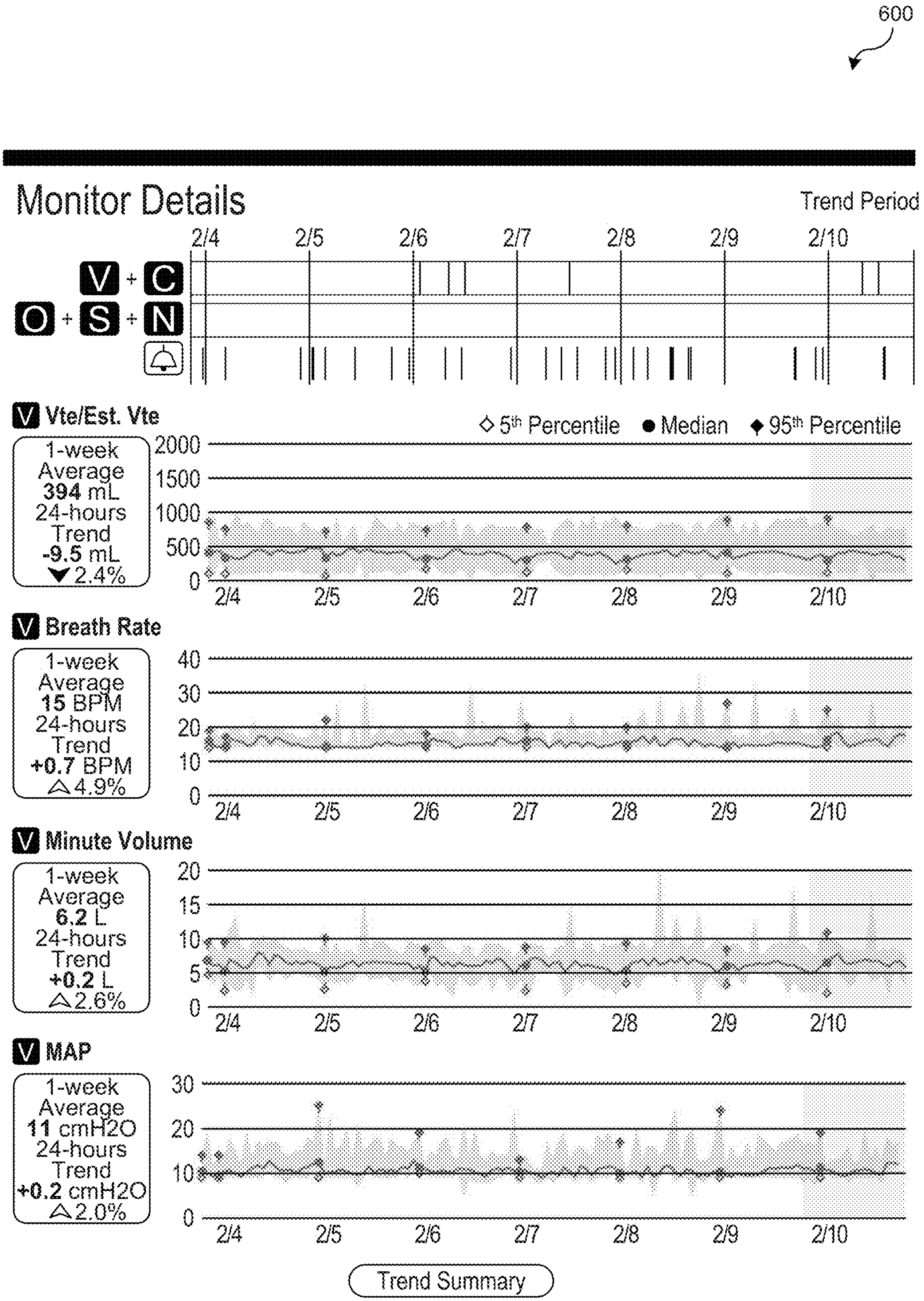
FIGS. 6A-6E illustrate an example monitor details report displaying simulated patient therapy data and generated in accordance with select embodiments of the present technology.
Figure 6B:
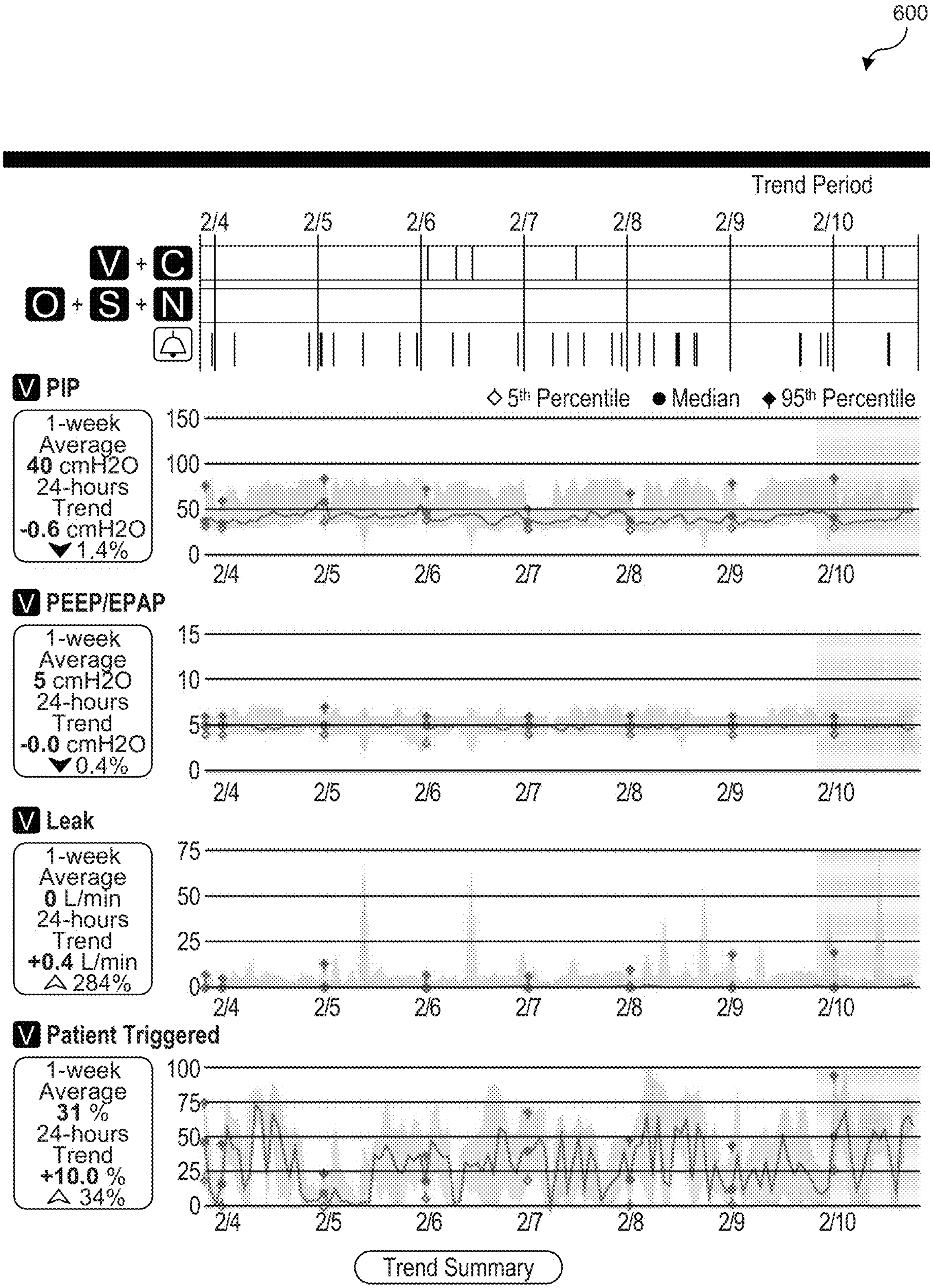
Figure 6C:
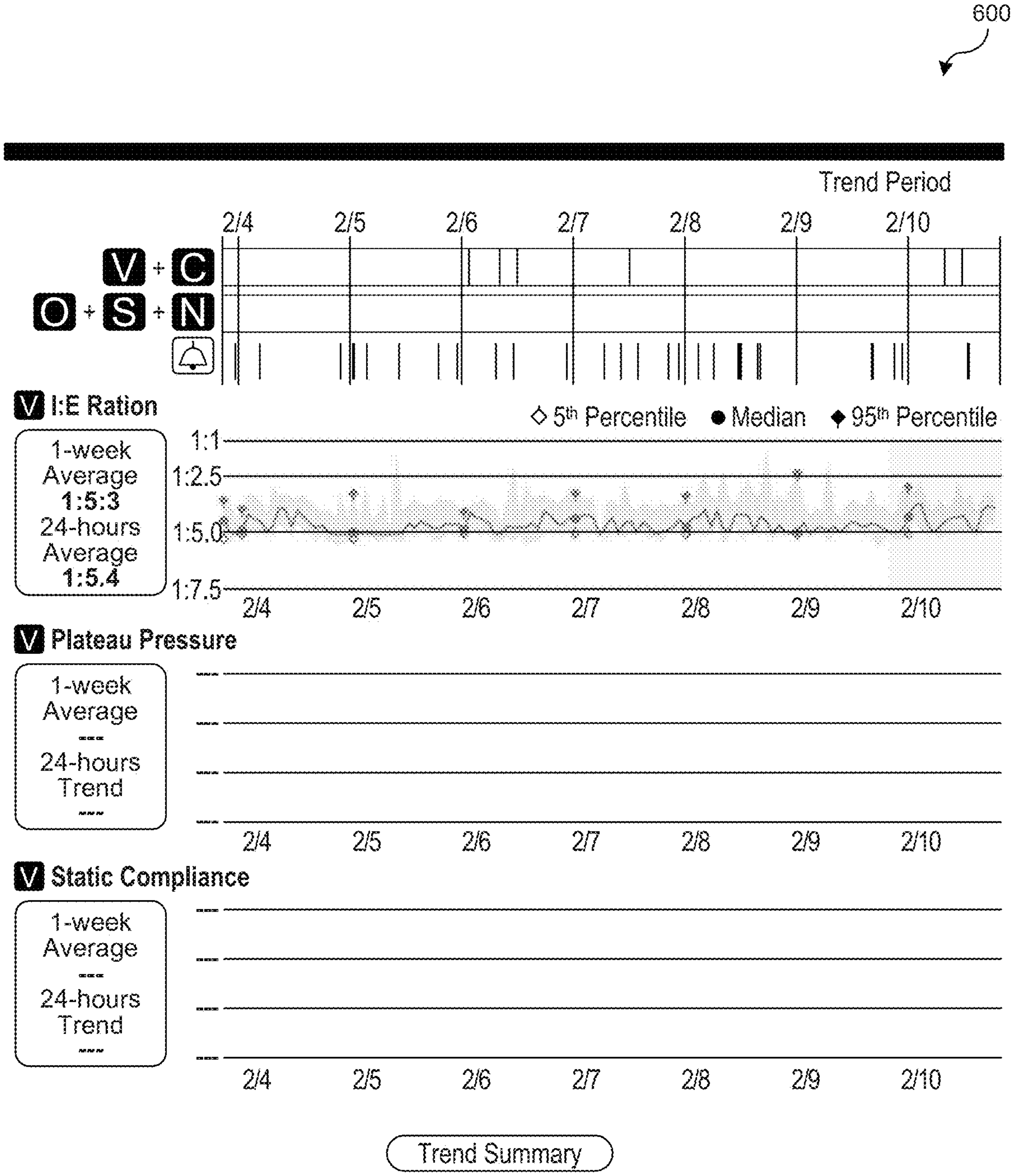
Figure 6D:
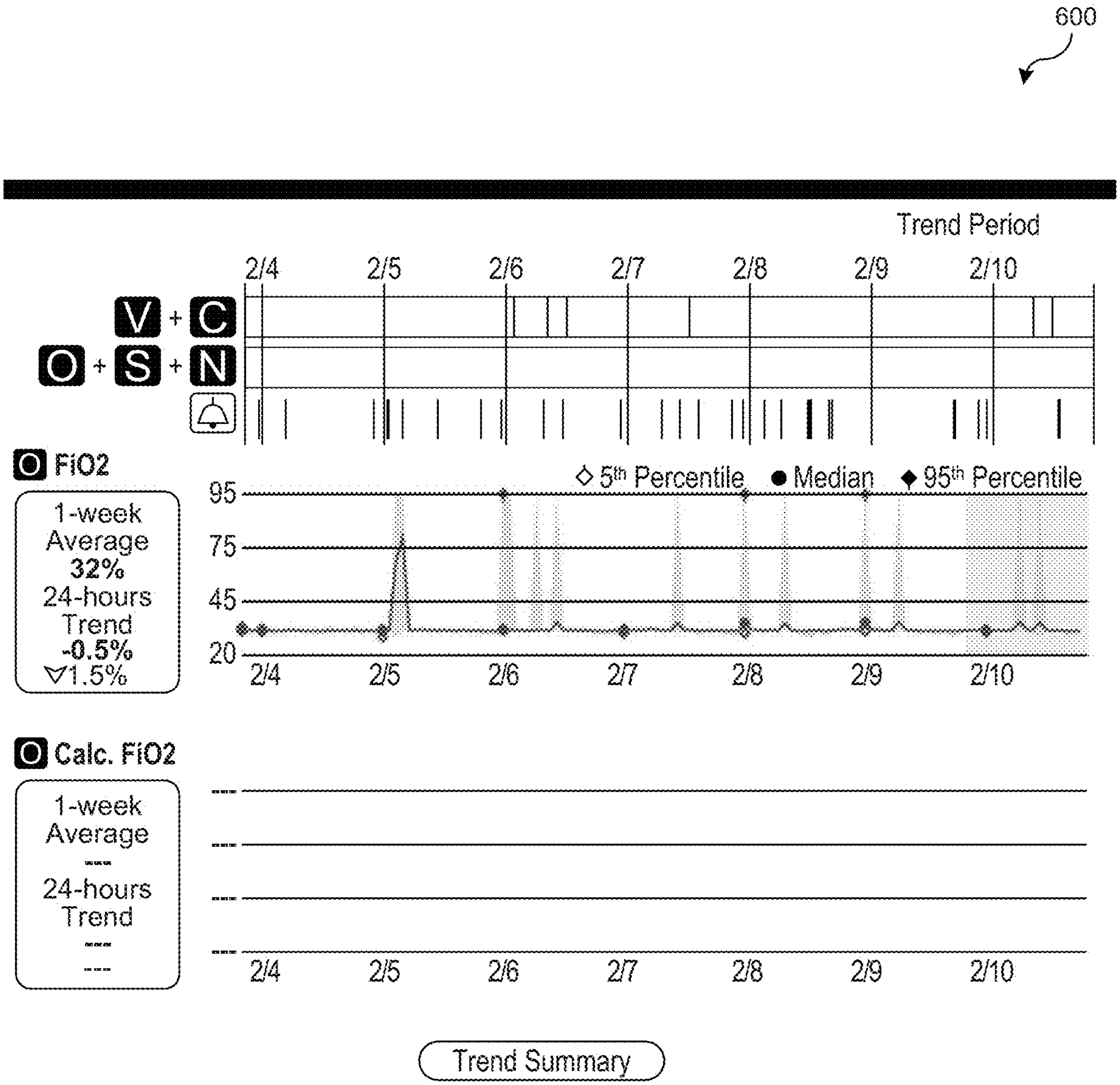
Figure 6E:
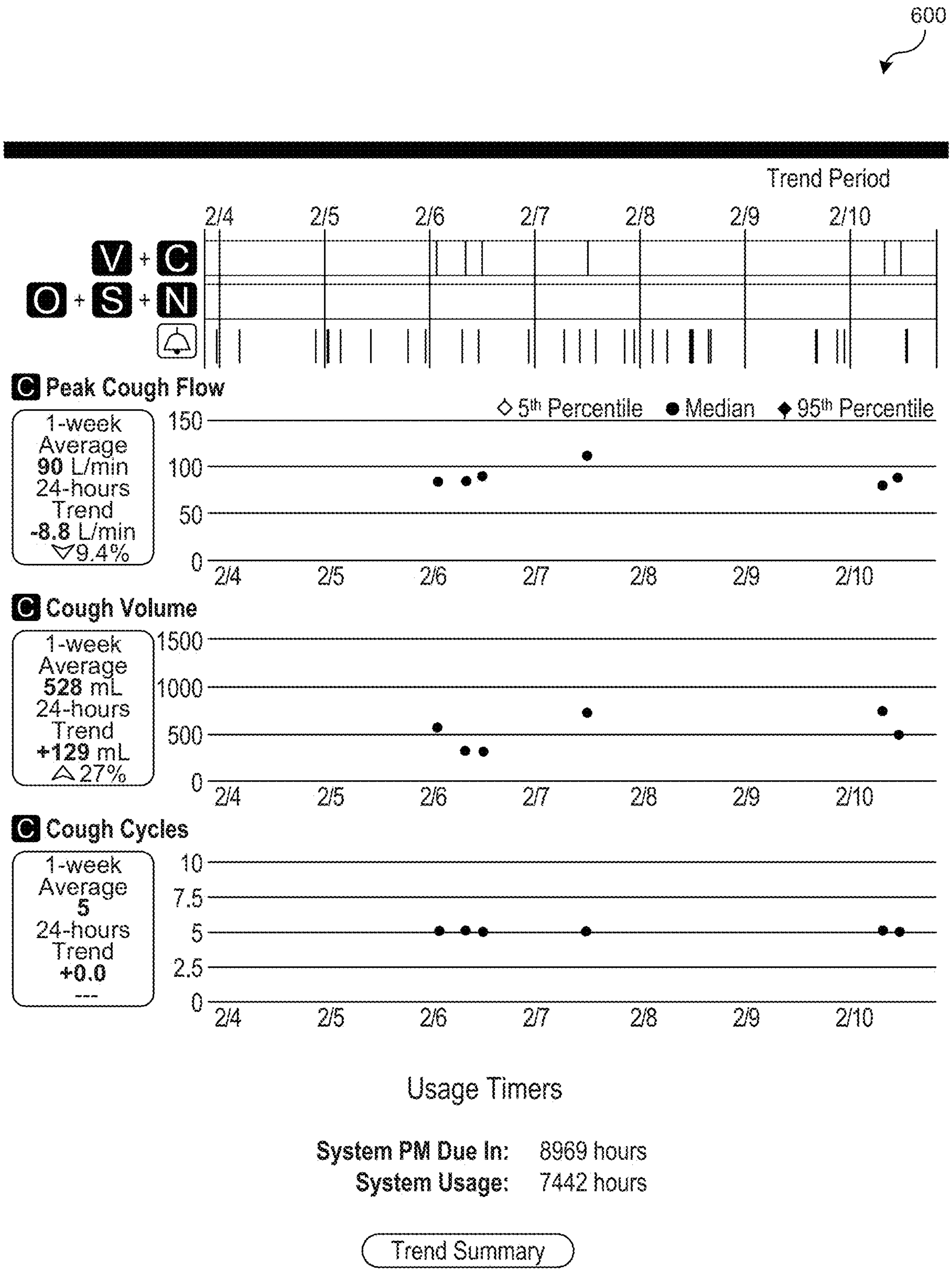

FIGS. 6A-6E illustrate example monitor details 600 that can also be included as part of a patient therapy report (e.g., the patient therapy report 259; FIG. 2) generated by the report generation module 258. The monitor details 600 can illustrate select patient and/or ventilator parameters associated with the various respiratory therapies. For example, FIGS. 6A-6C illustrate select parameters associated with a ventilation therapy V (e.g., breathing assistance provided by the ventilation module 202 of the ventilator 200; FIG. 2), FIG. 6D illustrates select parameters associated with an oxygen therapy O (e.g., oxygen provided by the oxygen module 206 of the ventilator 200), and FIG. 6E illustrates select parameters associated with a cough-assist therapy C (e.g., cough assistance provided by the cough-assist module 204).

FIG. 7 illustrates an example therapy log 700 that can also be included as part of a patient therapy report (e.g., the patient therapy report 259; FIG. 2) generated by the report generation module 258. The therapy log 700 can provide a list of each use of the various respiratory therapies, illustrating the start time/date, end time/date, and duration for each use each respiratory therapy. In some embodiments, the therapy log 700 can integrate other non-respiratory therapies into the same therapy log as the respiratory therapy log, such that the patient's use of both respiratory and non-respiratory therapies can be viewed as part of a single log.

As one skilled in the art will appreciate from the disclosure herein, FIGS. 3-7 are provided by way of example only. As previously described, the systems described herein can generate patient treatment reports having a variety of forms, data, presentations, modes (e.g., digital, print, interactive, etc.) and the like. Indeed, an expected advantage of the present technology is the ability to provide customizable patient treatment reports that provide comprehensive patient treatment data across multiple therapy modalities. Accordingly, the present technology is not limited by the examples provided herein, and includes other patient treatment reports generated in accordance with the description herein.

Figure 8:
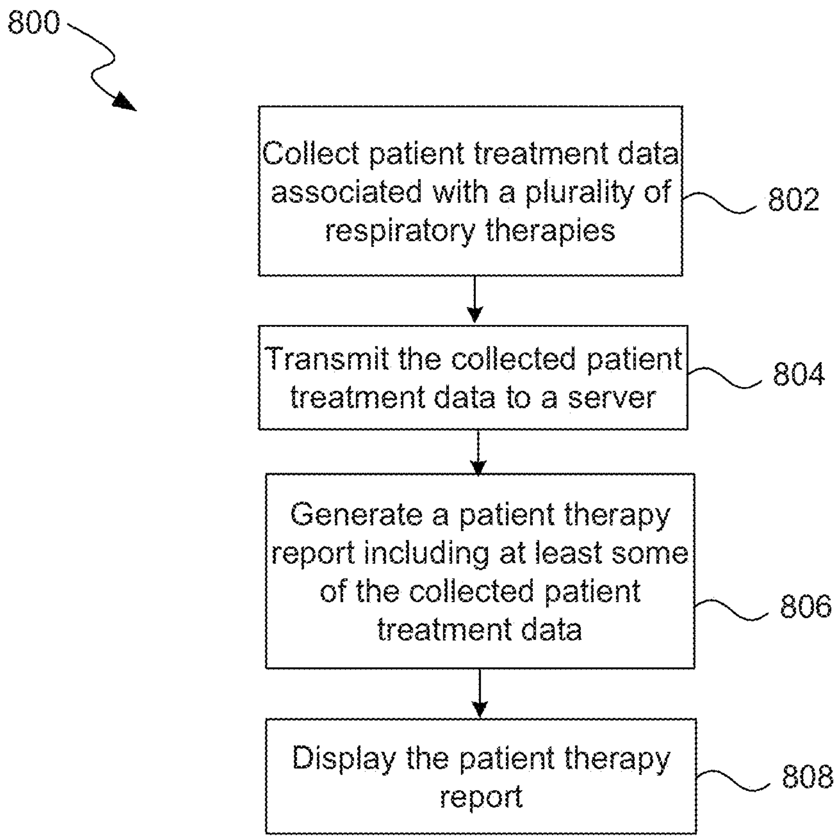
FIG. 8 is a flowchart of a method 800 for monitoring respiratory therapy administered to a patient in accordance with embodiments of the present technology.

FIG. 8 is a flowchart of a method 800 for monitoring respiratory therapy administered to a patient in accordance with embodiments of the present technology. The method 800 can begin in step 802 by collecting patient treatment data associated with a plurality of respiratory therapies. The respiratory therapies can include, but are not limited to, ventilation therapy, oxygen therapy, cough-assistance therapy, suction therapy, nebulization therapy, and any combinations thereof. The patient treatment data can include any of the patient treatment data previously described herein. In some embodiments, collecting the patient treatment data can include receiving the patient treatment data at a data transfer element (e.g., the data transfer element 230). In some embodiments, collecting the patient treatment data can include collecting the patient treatment data from a single respiratory device configured to deliver the plurality of respiratory therapies. In other embodiments, collecting the patient treatment data can include collecting the patient treatment data from a plurality of respiratory devices configured to deliver the plurality of respiratory therapies. In some embodiments, collecting the patient treatment data includes collecting patient treatment data from a plurality of patient monitors (e.g., a pulse oximeter, a blood pressure monitor, etc.) in addition to collecting patient treatment data from a respiratory device.

The method 800 can continue in step 804 by transmitting the collected patient treatment data to a server (e.g., the server 150). The patient treatment data can be transmitted via a wired or wireless connection, as previously described. In some embodiments, the patient treatment data is transmitted via the data transfer element (e.g., the data transfer element 230). The patient treatment data can be transmitted automatically and periodically (e.g., daily, weekly, once every two weeks, once per month, etc.), continuously, and/or on-demand and in response to a user request for the patient treatment data.

The method 800 can continue in step 806 by generating a patient therapy report including at least some of the patient treatment data collected in step 802. For example, the report generation module 258 of the server 250 can generate the patient therapy report. In some embodiments, step 806 is performed in response to receiving a user request to generate the patient report. In some embodiments, the generated user report is customized according to the user's preferences (e.g., as specified in the user request), as previously described.

The method 800 can continue in step 808 by displaying the patient therapy report. For example, the patient therapy report can be displayed on a digital display (e.g., display 276 on computing device 170) such that a healthcare provider or other user can review the contents of the report. In some embodiments, the patient therapy report is interactive, and the healthcare provider or other user can manipulate aspects of the report (e.g., view, scale, graph-type, etc.) of the report by interacting with the digital display.

The systems and methods described herein can be used to collect, store, monitor, report, and/or analyze patient treatment data for patients having a variety of indications. For example, the systems and methods may be used in conjunction with respiratory therapies provided to treat conditions such as neuromuscular diseases (e.g., muscular dystrophies, amyotrophic lateral sclerosis, etc.), impaired lung function (e.g., caused by COPD, cystic fibrosis, lung cancers, emphysema, viral infections, or other respiratory diseases), spinal cord injury, and pediatric development complication (e.g., premature birth, chronic lung disease, etc.).

As set forth herein, one expected advantage of the present technology is the ability to collect patient treatment data, including both respiratory data and non-respiratory therapy data, from multiple different devices/sources, and to provide a single comprehensive and customizable report for a particular patient. Another expected advantage is the ability for both the healthcare provider and the patient or patient's caregiver to access and review the patient treatment data, and/or to annotate or add comments to a summary of the patient treatment data. Of course, embodiments of the present technology may provide other advantages described throughout this Detailed Description, as well as other advantages not expressly disclosed herein. Accordingly, without being bound by theory, the present technology is therefore expected to improve patient care by, for example, enabling a patient's healthcare provider to review a comprehensive profile of a patient's therapy, provide recommended therapy adjustments, alert physicians to patient non-compliance, improve patient-physician communication, improve real-time and/or remote monitoring of a patient, and the like.

The systems and methods described herein can be implemented with and/or distributed across computing architecture. For example, many of the systems described herein include a memory storing data, software modules, instructions, or the like. The memories described herein can include one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory is a non-transitory computer-readable storage medium that stores, for example, programs, software, data, or the like.

As one of skill in the art will appreciate from the disclosure herein, various components of the systems described above can be omitted without deviating from the scope of the present technology. Likewise, additional components not explicitly described above may be added to the systems without deviating from the scope of the present technology. For example, it will be appreciated that specific embodiments of the technology have been described herein for purposes of illustration, but well-known structures and functions have not been shown or described in detail to avoid unnecessarily obscuring the description of the embodiments of the technology. Moreover, although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. Accordingly, the present technology is not limited to the configurations expressly identified herein, but rather encompasses variations and alterations of the described systems and methods.

Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Further, where specific integers are mentioned herein which have known equivalents in the art to which the embodiments relate, such known equivalents are deemed to be incorporated herein as if individually set forth.

We claim:

1. A method for analyzing and monitoring ventilation therapy and cough therapy provided to a patient, the method comprising:

providing a plurality of respiratory therapies to the patient using a ventilator with an integrated cough-assist module, wherein providing the plurality of respiratory therapies includes (a) delivering the ventilation therapy to the patient using the ventilator, and (b) providing the cough-assistance therapy to the patient using the cough-assist module;

collecting, in real time, patient treatment data associated with the ventilation therapy and the cough-assistance therapy, wherein the patient treatment data includes ventilation therapy data comprising one or more pressure waveforms, flow waveforms, and/or volume waveforms associated with the ventilation therapy, and cough-assistance therapy data comprising one or more of peak cough flow, cough volume, insufflation pressure, exsufflation pressure, insufflation time, exsufflation time, pause time, and/or insufflation rise time;

receiving a user request to view a live-stream of the ventilation therapy data and the cough-assistance therapy data at a computing device remote from the ventilator;

in response to receiving the user request, transmitting the ventilation therapy data and the cough-assistance therapy data from the ventilator to a remote server, wherein the server includes a patient data module storing patient treatment data associated with a plurality of patients, the plurality of patients including the patient;

comparing the ventilation therapy data and the cough-assistance therapy data received from the ventilator to historical ventilation therapy data and historical cough-assistance therapy data for the patient stored on patient data module;

based on the comparison, automatically calculating one or more trends associated with the ventilation therapy and/or the cough-assistance therapy;

displaying (c) the cough-assistance therapy data and the ventilation therapy data, including the one or more pressure waveforms, flow waveforms, and/or volume waveforms associated with the ventilation therapy, and (d) the one or more calculated trends associated with the ventilation therapy and/or the cough-assistance therapy, at the computing device, wherein a delay between collecting the ventilation therapy data and the cough-assistance therapy data at the ventilator and displaying the ventilation therapy data and the cough-assistance therapy data at the computing device is less than about 120 seconds such that the user can remotely monitor the ventilation therapy data and the cough-assistance therapy data in substantially real time; and adjusting at least one of the ventilation therapy or the cough-assistance therapy based at least in part on the displayed cough-assistance therapy data, the displayed ventilation therapy data, and/or the displayed calculated trends.

2. The method of claim 1 wherein collecting the patient treatment data includes receiving the patient treatment data at a data transfer element, and wherein transmitting the patient treatment data includes transmitting the patient treatment data from the data transfer element to the server.

3. The method of claim 2 wherein the data transfer element is coupled to a plurality of medical devices, the plurality of medical devices including the ventilator, and wherein receiving the patient treatment data at the data transfer element includes receiving the patient treatment data associated with the plurality of medical devices.

4. The method of claim 3 wherein the plurality of medical devices includes:

the ventilator with the integrated cough-assist module; and at least one secondary medical device, wherein the at least one secondary medical device includes a blood pressure monitor, a blood glucose monitor, a heart rate monitor, an $SpO_2$ monitor, a weight monitor, a carbon dioxide monitor, and/or a drug delivery device.

5. The method of claim 1, further comprising generating a patient therapy report, wherein the patient therapy report includes a graphical display of at least some of the patient treatment data transmitted to the server.

6. The method of claim 5, further comprising displaying, via a digital display, the patient therapy report.

7. The method of claim 6 wherein the patient therapy report is interactive.

8. The method of claim 6 wherein the patient therapy report is customized based on a user's preferences.

9. The method of claim 6, further comprising:

receiving, from a user, one or more annotations or markings to be added to the patient therapy report; and in response to receiving the one or more annotations or markings, adding the one or more annotations or markings to the patient therapy report.

10. The method of claim 1, further comprising analyzing the collected patient treatment data and providing one or more recommendations associated with at least one of the plurality of respiratory therapies, wherein adjusting at least one of the ventilation therapy or the cough-assistance therapy is based on the one or more recommendations.

11. The method of claim 1 wherein the patient treatment data is first patient treatment data, the method further comprising:

collecting second patient treatment data associated with a plurality of non-respiratory therapies used by the patient;

transmitting the second patient treatment data to the server; and generating a patient report including at least a subset of the first patient treatment data and a subset of the second patient treatment data.

12. A method for analyzing and monitoring ventilation therapy and cough therapy provided to a patient, the method comprising:

providing a plurality of respiratory therapies to the patient using a ventilator with an integrated cough-assist module, wherein providing the plurality of respiratory therapies includes (a) delivering the ventilation therapy to the patient using the ventilator, and (b) providing the cough-assistance therapy to the patient using the cough-assist module;

collecting patient treatment data associated with the ventilation therapy and the cough-assistance therapy, wherein the patient treatment data includes ventilation therapy data comprising one or more pressure waveforms, flow waveforms, and/or volume waveforms associated with the ventilation therapy, and cough-assistance therapy data comprising one or more of peak cough flow, cough volume, insufflation pressure, exsufflation pressure, insufflation time, exsufflation time, pause time, and/or insufflation rise time;

transmitting the ventilation therapy data and the cough-assistance therapy data from the ventilator to a server having a patient data module storing historical ventilation therapy data and historical cough-assistance therapy data for the patient;

accessing, via the server, the historical ventilation therapy data and the historical cough-assistance therapy data;

comparing the ventilation therapy data and the cough-assistance therapy data received from the ventilator to the historical ventilation therapy data and the historical cough-assistance therapy data;

based on the comparison, automatically calculating one or more trends associated with the ventilation therapy and/or the cough-assistance therapy;

displaying, via an electronic screen, (c) the cough-assistance therapy data and the ventilation therapy data, and (d) the one or more calculated trends associated with the ventilation therapy and/or the cough-assistance therapy; and adjusting at least one of the ventilation therapy or the cough-assistance therapy based at least in part on the displayed cough-assistance therapy data, the displayed ventilation therapy data, and/or the displayed calculated trends.

13. The method of claim 12, further comprising analyzing the collected patient treatment data and providing one or more recommendations associated with at least one of the plurality of respiratory therapies, wherein adjusting at least one of the ventilation therapy or the cough-assistance therapy is based on the one or more recommendations.

14. The method of claim 13 wherein the patient data module stores reference patient treatment data associated with a plurality of reference patients in addition to the patient treatment data, and wherein the one or more recommendations are based at least in part on the reference patient treatment data in addition to the patient treatment data.

15. The method of claim 12 wherein the electronic screen is interactive, and wherein the method further comprises:

receiving, from a user, one or more manipulations to the displayed cough-assistance therapy data, the displayed ventilation therapy data, and/or the displayed calculated trends, and updating the displayed cough-assistance therapy data, the displayed ventilation therapy data, and/or the displayed calculated trends, based on the one or more manipulations.

16. A method for analyzing and monitoring ventilation therapy and oxygen therapy provided to a patient, the method comprising:

providing a plurality of respiratory therapies to the patient using a ventilator with an integrated oxygen module, wherein providing the plurality of respiratory therapies includes (a) delivering the ventilation therapy to the patient using the ventilator, and (b) providing the oxygen therapy to the patient using the oxygen module;

collecting patient treatment data associated with the ventilation therapy and the oxygen therapy, wherein the patient treatment data includes ventilation therapy data comprising one or more pressure waveforms, flow waveforms, and/or volume waveforms associated with the ventilation therapy, and oxygen therapy data comprising one or more of oxygen delivery mode, oxygen flow equivalent, average FiO2 percentage, low $FiO_2$ percentage, and/or high $FiO_2$ percentage;

transmitting the ventilation therapy data and the oxygen therapy data from the ventilator to a server having a patient data module storing historical ventilation therapy data and historical oxygen therapy data for the patient;

accessing, via the server, the historical ventilation therapy data and historical oxygen therapy data;

comparing the ventilation therapy data and the oxygen therapy data received from the ventilator to historical ventilation therapy data and the historical oxygen therapy data;

based on the comparison, automatically calculating one or more trends associated with the ventilation therapy and/or the oxygen therapy;

displaying, via an electronic screen, (c) the oxygen therapy data and the ventilation therapy data, and (d) the one or more calculated trends associated with the ventilation therapy and/or the oxygen therapy; and adjusting at least one of the ventilation therapy or the oxygen therapy based at least in part on the displayed oxygen therapy data, the displayed ventilation therapy data, and/or the displayed calculated trends.

17. The method of claim 16, further comprising:

receiving a user request to view a live-stream of the ventilation therapy data and the oxygen therapy data at a computing device remote from the ventilator, wherein transmitting the ventilation therapy data and the oxygen therapy data from the ventilator to the server is performed automatically in response to receiving the user request, and wherein a delay between collecting the ventilation therapy data and the oxygen therapy data at the ventilator and displaying the ventilation therapy data and the oxygen therapy data at the computing device is less than about 120 seconds such that the user can remotely monitor the ventilation therapy data and the oxygen therapy data in substantially real time.

18. The method of claim 16, further comprising analyzing the collected patient treatment data and providing one or more recommendations associated with at least one of the plurality of respiratory therapies, wherein adjusting at least one of the ventilation therapy or the oxygen therapy is based on the one or more recommendations.

19. The method of claim 18 wherein the patient data module stores reference patient treatment data associated with a plurality of reference patients in addition to the patient treatment data, and wherein the one or more recommendations are based at least in part on the reference patient treatment data in addition to the patient treatment data.

20. The method of claim 16 wherein the electronic screen is interactive, and wherein the method further comprises:

receiving, from a user, one or more manipulations to the displayed oxygen therapy data, the displayed ventilation therapy data, and/or the displayed calculated trends, and updating the displayed oxygen therapy data, the displayed ventilation therapy data, and/or the displayed calculated trends, based on the one or more manipulations.

* * * * *